US008255030B2

(12) United States Patent
Petisce et al.

(10) Patent No.: US 8,255,030 B2
(45) Date of Patent: Aug. 28, 2012

(54) OXYGEN ENHANCING MEMBRANE SYSTEMS FOR IMPLANTABLE DEVICES

(75) Inventors: James Petisce, San Diego, CA (US); Mark A. Tapsak, Orangeville, PA (US); Peter C. Simpson, Del Mar, CA (US); Victoria Carr-Brendel, Pleasanton, CA (US); James H. Brauker, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 1890 days.

(21) Appl. No.: 11/410,555

(22) Filed: Apr. 25, 2006

(65) Prior Publication Data

US 2006/0189856 A1 Aug. 24, 2006

Related U.S. Application Data

(62) Division of application No. 10/896,639, filed on Jul. 21, 2004, now Pat. No. 7,379,765.

(51) Int. Cl.
*A61B 5/05* (2006.01)
*A61B 5/00* (2006.01)

(52) U.S. Cl. ......................... 600/345; 600/347; 600/365

(58) Field of Classification Search .................. 600/309, 600/345–366

See application file for complete search history.

(56) References Cited

U.S. PATENT DOCUMENTS 2,830,020 A 4/1958 Christmann et al.
3,220,960 A 11/1965 Drahoslav Lim et al.
3,562,352 A 2/1971 Nyilas
3,607,329 A 9/1971 Manjikian
3,746,588 A 7/1973 Brown, Jr.
3,898,984 A 8/1975 Mandel et al.
3,943,918 A 3/1976 Lewis
3,979,274 A 9/1976 Newman
4,003,621 A 1/1977 Lamp
4,040,908 A 8/1977 Clark, Jr.
4,073,713 A 2/1978 Newman
4,136,250 A 1/1979 Mueller et al.

(Continued)

FOREIGN PATENT DOCUMENTS

EP 0 098 592 1/1984

(Continued)

OTHER PUBLICATIONS

Abstract (English translation) of JP 2002055076-A, Matsumoto, Tatsu.

(Continued)

*Primary Examiner* — Navin Natnithithadha

(74) *Attorney, Agent, or Firm* — Knobbe, Martens, Olson & Bear, LLP.

(57) ABSTRACT

The present invention relates generally to systems and methods for increasing oxygen availability to implantable devices. The preferred embodiments provide a membrane system configured to provide protection of the device from the biological environment and/or a catalyst for enabling an enzymatic reaction, wherein the membrane system includes a polymer formed from a high oxygen soluble material. The high oxygen soluble polymer material is disposed adjacent to an oxygen-utilizing source on the implantable device so as to dynamically retain high oxygen availability to the oxygen-utilizing source during oxygen deficits. Membrane systems of the preferred embodiments are useful for implantable devices with oxygen-utilizing sources and/or that function in low oxygen environments, such as enzyme-based electrochemical sensors and cell transplantation devices.

21 Claims, 5 Drawing Sheets

50 48 46 44 42 40

18

U.S. PATENT DOCUMENTS 4,253,469 A 3/1981 Aslan
4,256,561 A 3/1981 Schindler et al.
4,260,725 A 4/1981 Keogh et al.
4,267,145 A 5/1981 Wysong
4,292,423 A 9/1981 Kaufmann et al.
4,374,013 A 2/1983 Enfors
4,403,984 A 9/1983 Ash et al.
4,415,666 A 11/1983 D'Orazio et al.
4,418,148 A 11/1983 Oberhardt
4,431,004 A 2/1984 Bessman et al.
4,431,507 A 2/1984 Nankai et al.
4,442,841 A 4/1984 Uehara et al.
4,454,295 A 6/1984 Wittmann et al.
4,482,666 A 11/1984 Reeves
4,484,987 A * 11/1984 Gough .......................... 205/778
4,493,714 A 1/1985 Ueda et al.
4,494,950 A 1/1985 Fischell
4,527,999 A 7/1985 Lee
4,545,382 A 10/1985 Higgins et al.
4,554,927 A 11/1985 Fussell
4,602,922 A 7/1986 Cabasso et al.
4,632,968 A 12/1986 Yokota et al.
4,644,046 A 2/1987 Yamada
4,647,643 A 3/1987 Zdrahala et al.
4,650,547 A 3/1987 Gough
4,671,288 A 6/1987 Gough
4,672,970 A 6/1987 Uchida et al.
4,680,268 A 7/1987 Clark, Jr.
4,684,538 A 8/1987 Klemarczyk
4,685,463 A 8/1987 Williams
4,686,044 A 8/1987 Behnke et al.
4,686,137 A 8/1987 Ward, Jr. et al.
4,689,149 A 8/1987 Kanno et al.
4,689,309 A 8/1987 Jones
4,703,756 A 11/1987 Gough et al.
4,711,245 A 12/1987 Higgins
4,721,677 A 1/1988 Clark, Jr.
4,726,381 A 2/1988 Jones
4,731,726 A 3/1988 Allen
4,739,380 A 4/1988 Lauks et al.
4,757,022 A 7/1988 Shults et al.
4,763,658 A 8/1988 Jones
4,781,733 A 11/1988 Babcock et al.
4,786,657 A 11/1988 Hammar et al.
4,793,555 A 12/1988 Lee et al.
4,795,542 A 1/1989 Ross et al.
4,803,243 A 2/1989 Fujimoto et al.
4,805,625 A 2/1989 Wyler
4,813,424 A 3/1989 Wilkins
4,822,336 A 4/1989 DiTraglia
4,832,034 A 5/1989 Pizziconi
4,849,458 A 7/1989 Reed et al.
4,852,573 A 8/1989 Kennedy
4,861,830 A 8/1989 Ward, Jr.
4,871,440 A 10/1989 Nagata et al.
4,880,883 A 11/1989 Grasel et al.
4,886,740 A 12/1989 Vadgama
4,890,620 A 1/1990 Gough
4,908,208 A 3/1990 Lee et al.
4,909,908 A 3/1990 Ross et al.
4,919,141 A 4/1990 Zier et al.
4,938,860 A 7/1990 Wogoman
4,951,657 A 8/1990 Pfister et al.
4,952,618 A 8/1990 Olsen
4,953,552 A 9/1990 DeMarzo
4,954,381 A 9/1990 Cabasso et al.
4,960,594 A 10/1990 Honeycutt
4,961,954 A 10/1990 Goldberg et al.
4,963,595 A 10/1990 Ward et al.
4,970,145 A 11/1990 Bennetto et al.
4,973,320 A 11/1990 Brenner et al.
4,988,341 A 1/1991 Columbus et al.
4,994,167 A 2/1991 Shults et al.
5,002,590 A 3/1991 Friesen et al.
5,010,141 A 4/1991 Mueller
5,030,333 A 7/1991 Clark, Jr.
5,034,461 A 7/1991 Lai et al.
5,045,601 A 9/1991 Capelli et al.
5,050,612 A 9/1991 Matsumura
5,063,081 A 11/1991 Cozzette et al.
5,070,169 A 12/1991 Robertson et al.
5,071,452 A 12/1991 Avrillon et al.
5,094,876 A 3/1992 Goldberg et al.
5,100,689 A 3/1992 Goldberg et al.
5,108,819 A 4/1992 Heller et al.
5,115,056 A 5/1992 Mueller et al.
5,120,813 A 6/1992 Ward, Jr.
5,128,408 A 7/1992 Tanaka et al.
5,135,297 A 8/1992 Valint et al.
5,137,028 A 8/1992 Nishimura
5,140,985 A 8/1992 Schroeder et al.
5,147,725 A 9/1992 Pinchuk
5,155,149 A 10/1992 Atwater et al.
5,160,418 A 11/1992 Mullen
5,165,407 A 11/1992 Wilson et al.
5,169,906 A 12/1992 Cray et al.
5,171,689 A 12/1992 Kawaguri et al.
5,183,549 A 2/1993 Joseph et al.
5,200,051 A 4/1993 Cozzette et al.
5,202,261 A 4/1993 Musho et al.
5,208,313 A 5/1993 Krishnan
5,212,050 A 5/1993 Mier et al.
5,219,965 A 6/1993 Valint et al.
5,221,724 A 6/1993 Li et al.
5,235,003 A 8/1993 Ward et al.
5,242,835 A 9/1993 Jensen
5,249,576 A 10/1993 Goldberger et al.
5,250,439 A 10/1993 Musho et al.
5,262,305 A 11/1993 Heller et al.
5,264,104 A 11/1993 Gregg et al.
5,269,891 A 12/1993 Colin
5,284,140 A 2/1994 Allen et al.
5,286,364 A 2/1994 Yacynych et al.
5,296,144 A 3/1994 Sternina et al.
5,299,571 A 4/1994 Mastrototaro
5,302,440 A 4/1994 Davis
5,316,008 A 5/1994 Suga et al.
5,322,063 A * 6/1994 Allen et al. ................... 600/347
5,324,322 A 6/1994 Grill et al.
5,331,555 A 7/1994 Hashimoto et al.
5,334,681 A 8/1994 Mueller et al.
5,336,102 A 8/1994 Cairns et al.
5,342,693 A 8/1994 Winters et al.
5,352,348 A 10/1994 Young et al.
5,372,133 A 12/1994 Hogen Esch
5,376,400 A 12/1994 Goldberg et al.
5,384,028 A 1/1995 Ito
5,387,327 A 2/1995 Khan
5,387,329 A * 2/1995 Foos et al. ................ 204/403.06
5,390,671 A 2/1995 Lord et al.
5,391,250 A 2/1995 Cheney, II et al.
5,397,451 A 3/1995 Senda et al.
5,397,848 A 3/1995 Yang et al.
5,401,376 A * 3/1995 Foos et al. ................ 204/403.06
5,411,866 A 5/1995 Luong
5,426,158 A 6/1995 Mueller et al.
5,428,123 A 6/1995 Ward et al.
5,429,735 A 7/1995 Johnson et al.
5,438,984 A 8/1995 Schoendorfer
5,453,248 A 9/1995 Olstein
5,458,631 A 10/1995 Xavier
5,462,051 A 10/1995 Oka et al.
5,466,575 A 11/1995 Cozzette et al.
5,469,846 A 11/1995 Khan
5,476,094 A 12/1995 Allen et al.
5,482,473 A 1/1996 Lord et al.
5,494,562 A 2/1996 Maley et al.
5,497,772 A 3/1996 Schulman et al.
5,503,719 A * 4/1996 Foos et al. .................. 205/782.5
5,507,288 A 4/1996 Bocker et al.
5,513,636 A 5/1996 Palti
5,518,601 A * 5/1996 Foos et al. ..................... 204/415
5,521,273 A 5/1996 Yilgor et al.
5,531,878 A 7/1996 Vadgama et al.
5,541,305 A 7/1996 Yokota et al.
5,552,112 A 9/1996 Schiffmann et al.
5,554,339 A 9/1996 Cozzette et al.

5,564,439 A 10/1996 Picha
5,568,806 A 10/1996 Cheney, II et al.
5,569,186 A 10/1996 Lord et al.
5,575,930 A 11/1996 Tietje-Girault et al.
5,582,184 A 12/1996 Erickson et al.
5,584,813 A 12/1996 Livingston et al.
5,584,876 A 12/1996 Bruchman et al.
5,586,553 A 12/1996 Halili et al.
5,589,563 A 12/1996 Ward et al.
5,590,651 A 1/1997 Shaffer et al.
5,593,852 A 1/1997 Heller et al.
5,595,646 A * 1/1997 Foos et al. .................... 205/783
5,605,152 A 2/1997 Slate et al.
5,611,900 A 3/1997 Worden
5,624,537 A 4/1997 Turner et al.
5,631,340 A 5/1997 Olstein
5,640,954 A 6/1997 Pfeiffer
5,665,222 A 9/1997 Heller et al.
5,670,097 A 9/1997 Duan et al.
5,695,623 A 12/1997 Michel et al.
5,700,559 A 12/1997 Sheu et al.
5,702,823 A * 12/1997 Forrestal et al. .............. 428/450
5,703,359 A 12/1997 Wampler, III
5,711,861 A 1/1998 Ward et al.
5,738,902 A * 4/1998 Forrestal et al. ............. 427/2.12
5,741,330 A 4/1998 Brauker et al.
5,743,262 A 4/1998 Lepper, Jr. et al.
5,746,898 A 5/1998 Preidel
5,756,632 A 5/1998 Ward et al.
5,760,155 A 6/1998 Mowrer et al.
5,766,839 A 6/1998 Johnson et al.
5,773,270 A 6/1998 D'Orazio et al.
5,776,324 A 7/1998 Usala
5,777,060 A * 7/1998 Van Antwerp .................. 528/28
5,783,054 A 7/1998 Raguse et al.
5,786,439 A 7/1998 Van Antwerp et al.
5,791,344 A 8/1998 Schulman et al.
5,795,453 A 8/1998 Gilmartin
5,795,774 A 8/1998 Matsumoto et al.
5,800,420 A 9/1998 Gross
5,804,048 A 9/1998 Wong et al.
5,807,375 A 9/1998 Gross et al.
5,807,636 A 9/1998 Sheu et al.
5,811,487 A 9/1998 Schulz, Jr. et al.
5,820,570 A 10/1998 Erickson
5,820,589 A 10/1998 Torgerson et al.
5,834,583 A 11/1998 Hancock et al.
5,837,377 A 11/1998 Sheu et al.
5,837,454 A 11/1998 Cozzette et al.
5,837,661 A 11/1998 Evans et al.
5,843,069 A 12/1998 Butler et al.
5,863,972 A 1/1999 Beckelmann et al.
5,882,494 A 3/1999 Van Antwerp
5,885,566 A 3/1999 Goldberg
5,897,955 A 4/1999 Drumheller
5,914,026 A 6/1999 Blubaugh, Jr. et al.
5,914,182 A 6/1999 Drumheller
5,931,814 A 8/1999 Alex et al.
5,932,299 A 8/1999 Katoot
5,945,498 A 8/1999 Hopken et al.
5,947,127 A 9/1999 Tsugaya et al.
5,954,643 A 9/1999 Van Antwerp et al.
5,955,066 A 9/1999 Sako et al.
5,957,854 A 9/1999 Besson et al.
5,959,191 A 9/1999 Lewis et al.
5,961,451 A 10/1999 Reber et al.
5,964,745 A 10/1999 Lyles et al.
5,964,993 A * 10/1999 Blubaugh et al. ........ 204/403.09
5,965,380 A 10/1999 Heller et al.
5,969,076 A 10/1999 Lai et al.
5,972,199 A 10/1999 Heller
5,972,369 A 10/1999 Roorda et al.
5,977,241 A 11/1999 Koloski et al.
5,985,129 A 11/1999 Gough et al.
6,001,067 A 12/1999 Shults et al.
6,002,954 A 12/1999 Van Antwerp et al.
6,007,845 A 12/1999 Domb
6,011,984 A 1/2000 Van Antwerp et al.
6,015,572 A 1/2000 Lin et al.
6,018,013 A 1/2000 Yoshida et al.
6,018,033 A 1/2000 Chen et al.
6,022,463 A 2/2000 Leader et al.
6,030,827 A 2/2000 Davis et al.
6,039,913 A 3/2000 Hirt et al.
6,043,328 A 3/2000 Domschke et al.
6,051,389 A 4/2000 Ahl et al.
6,059,946 A 5/2000 Yukawa et al.
6,066,448 A 5/2000 Wohlstadter et al.
6,071,406 A 6/2000 Tsou
6,081,736 A 6/2000 Colvin et al.
6,083,523 A 7/2000 Dionne et al.
6,083,710 A 7/2000 Heller et al.
6,088,608 A 7/2000 Schulman et al.
6,091,975 A 7/2000 Daddona et al.
6,093,172 A 7/2000 Funderburk et al.
6,107,083 A 8/2000 Collins et al.
6,119,028 A 9/2000 Schulman et al.
6,121,009 A 9/2000 Heller et al.
6,122,536 A 9/2000 Sun et al.
6,134,461 A 10/2000 Say et al.
6,141,573 A 10/2000 Kurnik et al.
6,162,611 A 12/2000 Heller et al.
6,175,752 B1 1/2001 Say et al.
6,200,772 B1 3/2001 Vadgama et al.
6,212,416 B1 4/2001 Ward et al.
6,233,471 B1 5/2001 Berner et al.
6,248,067 B1 6/2001 Causey, III et al.
6,256,522 B1 7/2001 Schultz
6,259,937 B1 7/2001 Schulman et al.
6,264,825 B1 7/2001 Blackburn et al.
6,271,332 B1 8/2001 Lohmann et al.
6,275,717 B1 8/2001 Gross et al.
6,284,478 B1 9/2001 Heller et al.
6,303,670 B1 10/2001 Fujino et al.
6,306,594 B1 10/2001 Cozzette et al.
6,312,706 B1 11/2001 Lai et al.
6,329,161 B1 12/2001 Heller et al.
6,329,488 B1 12/2001 Terry et al.
6,343,225 B1 1/2002 Clark, Jr.
6,358,557 B1 3/2002 Wang et al.
6,368,658 B1 4/2002 Schwarz et al.
6,372,020 B2 * 4/2002 Hong et al. ...................... 95/54
6,372,244 B1 4/2002 Antanavich et al.
6,387,379 B1 5/2002 Goldberg et al.
6,400,974 B1 6/2002 Lesho
6,405,066 B1 6/2002 Essenpreis et al.
6,407,195 B2 6/2002 Sherman et al.
6,413,393 B1 7/2002 Van Antwerp et al.
6,413,396 B1 7/2002 Yang et al.
6,424,847 B1 7/2002 Mastrototaro et al.
6,442,413 B1 8/2002 Silver
6,461,496 B1 10/2002 Feldman et al.
6,466,810 B1 10/2002 Ward et al.
6,477,395 B2 11/2002 Schulman et al.
6,484,046 B1 11/2002 Say et al.
6,512,939 B1 1/2003 Colvin et al.
6,514,718 B2 2/2003 Heller et al.
6,528,584 B2 3/2003 Kennedy et al.
6,541,107 B1 4/2003 Zhong et al.
6,545,085 B2 4/2003 Kilgour et al.
6,551,496 B1 4/2003 Moles et al.
6,554,982 B1 4/2003 Shin et al.
6,558,321 B1 5/2003 Burd et al.
6,565,509 B1 5/2003 Say et al.
6,579,498 B1 6/2003 Eglise
6,595,919 B2 7/2003 Berner et al.
6,596,294 B2 7/2003 Lai et al.
6,613,379 B2 9/2003 Ward et al.
6,618,934 B1 9/2003 Feldman et al.
6,633,772 B2 10/2003 Ford et al.
6,642,015 B2 11/2003 Vachon et al.
6,654,625 B1 11/2003 Say et al.
6,666,821 B2 * 12/2003 Keimel ........................ 600/365
6,670,115 B1 12/2003 Zhang
6,689,265 B2 2/2004 Heller et al.
6,692,528 B2 2/2004 Ward et al.
6,702,857 B2 3/2004 Brauker et al.
6,702,972 B1 3/2004 Markle 6,721,587 B2 * 4/2004 Gough .......... 600/345
6,740,059 B2 5/2004 Flaherty
6,741,877 B1 5/2004 Shults et al.
6,784,274 B2 8/2004 van Antwerp et al.
6,789,634 B1 9/2004 Denton
6,793,789 B2 9/2004 Choi et al.
6,801,041 B2 10/2004 Karinka et al.
6,802,957 B2 10/2004 Jung et al.
6,815,186 B2 11/2004 Clark, Jr.
6,858,218 B2 2/2005 Lai et al.
6,862,465 B2 3/2005 Shults et al.
6,867,262 B1 3/2005 Angel et al.
6,875,386 B1 * 4/2005 Ward et al. .......... 264/154
6,881,551 B2 4/2005 Heller et al.
6,895,263 B2 5/2005 Shin et al.
6,895,265 B2 5/2005 Silver
6,908,681 B2 6/2005 Terry et al.
6,932,894 B2 8/2005 Mao et al.
6,934,572 B2 8/2005 Schulman et al.
6,965,791 B1 11/2005 Hitchcock et al.
6,969,451 B2 11/2005 Shin et al.
6,973,706 B2 12/2005 Say et al.
7,008,979 B2 3/2006 Schottman et al.
7,014,948 B2 3/2006 Lee et al.
7,033,322 B2 4/2006 Silver
7,052,131 B2 5/2006 McCabe et al.
7,074,307 B2 7/2006 Simpson et al.
7,108,778 B2 9/2006 Simpson et al.
7,110,803 B2 9/2006 Shults et al.
7,118,667 B2 10/2006 Lee
7,120,483 B2 10/2006 Russell et al.
7,136,689 B2 11/2006 Shults et al.
7,153,265 B2 12/2006 Vachon
7,157,528 B2 1/2007 Ward
7,172,075 B1 2/2007 Ji
7,192,450 B2 3/2007 Brauker et al.
7,226,978 B2 6/2007 Tapsak et al.
7,229,471 B2 6/2007 Gale et al.
7,241,586 B2 7/2007 Gulati
7,248,906 B2 7/2007 Dirac et al.
7,279,174 B2 10/2007 Pacetti et al.
7,303,814 B2 * 12/2007 Lamberti et al. .......... 428/357
7,335,286 B2 2/2008 Abel et al.
7,336,984 B2 * 2/2008 Gough et al. .......... 600/345
7,357,793 B2 4/2008 Pacetti
7,366,556 B2 4/2008 Brister et al.
7,379,765 B2 5/2008 Petisce et al.
7,417,164 B2 8/2008 Suri
7,423,074 B2 9/2008 Lai et al.
7,470,488 B2 12/2008 Lee et al.
7,507,579 B2 * 3/2009 Boccazzi et al. .......... 435/297.5
7,534,330 B2 * 5/2009 Yu et al. .......... 204/403.11
7,651,596 B2 1/2010 Petisce et al.
7,711,402 B2 * 5/2010 Shults et al. .......... 600/347
7,792,562 B2 * 9/2010 Shults et al. .......... 600/347
7,799,191 B2 * 9/2010 Yu et al. .......... 204/403.11
7,835,777 B2 * 11/2010 Shults et al. .......... 600/347
7,860,545 B2 * 12/2010 Shults et al. .......... 600/347
7,970,448 B2 * 6/2011 Shults et al. .......... 600/345
2002/0018843 A1 2/2002 Van Antwerp et al.
2002/0043471 A1 4/2002 Ikeda et al.
2002/0055673 A1 5/2002 Van Antwerp et al.
2002/0120186 A1 * 8/2002 Keimel .......... 600/365
2002/0123087 A1 9/2002 Vachon et al.
2002/0128546 A1 9/2002 Silver
2002/0156355 A1 10/2002 Gough
2002/0185384 A1 12/2002 Leong et al.
2002/0193885 A1 12/2002 Legeay et al.
2003/0006669 A1 1/2003 Pei et al.
2003/0009093 A1 1/2003 Silver
2003/0023317 A1 1/2003 Brauker et al.
2003/0032874 A1 2/2003 Rhodes et al.
2003/0059631 A1 3/2003 Al-Lamee
2003/0065254 A1 4/2003 Schulman et al.
2003/0069383 A1 4/2003 Van Antwerp et al.
2003/0088166 A1 5/2003 Say et al.
2003/0096424 A1 5/2003 Mao et al.
2003/0104273 A1 6/2003 Lee et al.
2003/0125498 A1 7/2003 McCabe et al.
2003/0132227 A1 7/2003 Geisler et al.
2003/0134100 A1 7/2003 Mao et al.
2003/0134347 A1 7/2003 Heller et al.
2003/0157409 A1 8/2003 Huang
2003/0181794 A1 9/2003 Rini et al.
2003/0199745 A1 10/2003 Burson et al.
2003/0199878 A1 10/2003 Pohjonen et al.
2003/0203991 A1 10/2003 Schottman et al.
2003/0211050 A1 11/2003 Majeti et al.
2003/0217966 A1 11/2003 Tapsak et al.
2003/0225324 A1 12/2003 Anderson et al.
2003/0228681 A1 12/2003 Ritts et al.
2003/0235817 A1 12/2003 Bartkowiak et al.
2004/0006263 A1 1/2004 Anderson et al.
2004/0011671 A1 1/2004 Shults et al.
2004/0045879 A1 3/2004 Shults et al.
2004/0063167 A1 4/2004 Kaastrup et al.
2004/0074785 A1 4/2004 Holker
2004/0077075 A1 * 4/2004 Jensen et al. .......... 435/297.2
2004/0084306 A1 5/2004 Shin et al.
2004/0106741 A1 6/2004 Kriesel et al.
2004/0106857 A1 6/2004 Gough
2004/0111017 A1 6/2004 Say et al.
2004/0111144 A1 6/2004 Lawin et al.
2004/0120848 A1 6/2004 Teodorczyk
2004/0138543 A1 7/2004 Russell et al.
2004/0143173 A1 7/2004 Reghabi et al.
2004/0167801 A1 8/2004 Say et al.
2004/0176672 A1 9/2004 Silver et al.
2004/0180391 A1 9/2004 Gratzl et al.
2004/0186362 A1 9/2004 Brauker et al.
2004/0213985 A1 10/2004 Lee et al.
2004/0224001 A1 11/2004 Pacetti et al.
2004/0228902 A1 11/2004 Benz
2004/0234575 A1 11/2004 Horres et al.
2005/0013842 A1 1/2005 Qiu et al.
2005/0027180 A1 2/2005 Goode et al.
2005/0027181 A1 2/2005 Goode et al.
2005/0027463 A1 2/2005 Goode et al.
2005/0031689 A1 2/2005 Shults et al.
2005/0033132 A1 2/2005 Shults et al.
2005/0043598 A1 2/2005 Goode et al.
2005/0044088 A1 2/2005 Lindsay et al.
2005/0051427 A1 3/2005 Brauker et al.
2005/0051440 A1 3/2005 Simpson et al.
2005/0054909 A1 3/2005 Petisce et al.
2005/0056552 A1 3/2005 Simpson et al.
2005/0070770 A1 3/2005 Dirac et al.
2005/0077584 A1 4/2005 Uhland et al.
2005/0079200 A1 4/2005 Rathenow et al.
2005/0089993 A1 * 4/2005 Boccazzi et al. .......... 435/286.2
2005/0090607 A1 4/2005 Tapsak et al.
2005/0107677 A1 5/2005 Ward et al.
2005/0112169 A1 5/2005 Brauker et al.
2005/0112172 A1 5/2005 Pacetti
2005/0112358 A1 5/2005 Potyrailo et al.
2005/0115832 A1 6/2005 Simpson et al.
2005/0118344 A1 6/2005 Pacetti
2005/0119720 A1 6/2005 Gale et al.
2005/0121322 A1 6/2005 Say
2005/0124873 A1 6/2005 Shults et al.
2005/0139489 A1 6/2005 Davies et al.
2005/0154272 A1 7/2005 Dirac et al.
2005/0173245 A1 8/2005 Feldman et al.
2005/0176136 A1 8/2005 Burd et al.
2005/0176678 A1 8/2005 Horres et al.
2005/0177036 A1 8/2005 Shults et al.
2005/0184641 A1 8/2005 Armitage et al.
2005/0192557 A1 9/2005 Brauker et al.
2005/0196747 A1 9/2005 Stiene
2005/0197554 A1 9/2005 Polcha
2005/0209665 A1 9/2005 Hunter et al.
2005/0233407 A1 10/2005 Pamidi et al.
2005/0239154 A1 10/2005 Feldman et al.
2005/0242479 A1 11/2005 Petisce et al.
2005/0245795 A1 11/2005 Goode et al.
2005/0245799 A1 11/2005 Brauker et al.
2005/0251083 A1 11/2005 Carr-Brendel et al.
2005/0266582 A1 * 12/2005 Modlin et al. .......... 436/164

2005/0271546 A1 12/2005 Gerber et al.
2005/0274665 A1 12/2005 Heilmann et al.
2005/0282997 A1 12/2005 Ward et al.
2006/0003398 A1 1/2006 Heller et al.
2006/0007391 A1 1/2006 McCabe et al.
2006/0008370 A1 1/2006 Massaro et al.
2006/0015020 A1 1/2006 Neale et al.
2006/0016700 A1 1/2006 Brister et al.
2006/0019327 A1 1/2006 Brister et al.
2006/0020186 A1 1/2006 Brister et al.
2006/0020187 A1 1/2006 Brister et al.
2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0040402 A1 2/2006 Brauker et al.
2006/0047095 A1 3/2006 Pacetti
2006/0058868 A1 3/2006 Gale et al.
2006/0065527 A1 3/2006 Samproni
2006/0067908 A1 3/2006 Ding
2006/0068208 A1 3/2006 Tapsak et al.
2006/0078908 A1 4/2006 Pitner et al.
2006/0079740 A1 4/2006 Silver et al.
2006/0086624 A1 4/2006 Tapsak et al.
2006/0134165 A1 6/2006 Pacetti
2006/0142524 A1 6/2006 Lai et al.
2006/0142525 A1 6/2006 Lai et al.
2006/0142526 A1 6/2006 Lai et al.
2006/0142651 A1 6/2006 Brister et al.
2006/0148985 A1 7/2006 Karthauser
2006/0155180 A1 7/2006 Brister et al.
2006/0159718 A1 7/2006 Rathenow et al.
2006/0159981 A1 7/2006 Heller
2006/0171980 A1 8/2006 Helmus et al.
2006/0177379 A1 8/2006 Asgari
2006/0183178 A1 8/2006 Gulati
2006/0183871 A1 8/2006 Ward et al.
2006/0189856 A1 8/2006 Petisce et al.
2006/0195029 A1 8/2006 Shults et al.
2006/0198864 A1 9/2006 Shults et al.
2006/0200019 A1 9/2006 Petisce et al.
2006/0200970 A1 9/2006 Brister et al.
2006/0204536 A1 9/2006 Shults et al.
2006/0229512 A1 10/2006 Petisce et al.
2006/0249381 A1 11/2006 Petisce et al.
2006/0249446 A1 11/2006 Yeager
2006/0249447 A1 11/2006 Yeager
2006/0252027 A1 11/2006 Petisce et al.
2006/0253012 A1 11/2006 Petisce et al.
2006/0258761 A1 11/2006 Boock et al.
2006/0258929 A1 11/2006 Goode et al.
2006/0263673 A1 11/2006 Kim et al.
2006/0263839 A1 11/2006 Ward et al.
2006/0269586 A1 11/2006 Pacetti
2006/0275857 A1 12/2006 Kjaer et al.
2006/0275859 A1 12/2006 Kjaer
2006/0289307 A1* 12/2006 Yu et al. .................. 204/403.01
2006/0293487 A1 12/2006 Gaymans et al.
2007/0003588 A1 1/2007 Chinn et al.
2007/0007133 A1 1/2007 Mang et al.
2007/0027385 A1 2/2007 Brister et al.
2007/0032717 A1 2/2007 Brister et al.
2007/0032718 A1 2/2007 Shults et al.
2007/0038044 A1 2/2007 Dobbles et al.
2007/0045902 A1 3/2007 Brauker et al.
2007/0059196 A1 3/2007 Brister et al.
2007/0123963 A1 5/2007 Krulevitch
2007/0129524 A1 6/2007 Sunkara
2007/0135698 A1 6/2007 Shah et al.
2007/0142584 A1 6/2007 Schorzman et al.
2007/0155851 A1 7/2007 Alli et al.
2007/0161769 A1 7/2007 Schorzman et al.
2007/0163880 A1 7/2007 Woo et al.
2007/0166343 A1 7/2007 Goerne et al.
2007/0166364 A1 7/2007 Beier et al.
2007/0173709 A1 7/2007 Petisce et al.
2007/0173710 A1 7/2007 Petisce et al.
2007/0197890 A1 8/2007 Boock et al.
2007/0200267 A1 8/2007 Tsai
2007/0202562 A1 8/2007 Curry
2007/0203568 A1 8/2007 Gale et al.
2007/0213611 A1 9/2007 Simpson et al.
2007/0215491 A1 9/2007 Heller et al.
2007/0218097 A1 9/2007 Heller et al.
2007/0227907 A1 10/2007 Shah et al.
2007/0229757 A1 10/2007 McCabe et al.
2007/0233013 A1 10/2007 Schoenberg
2007/0235331 A1 10/2007 Simpson et al.
2007/0242215 A1 10/2007 Schorzman et al.
2007/0244379 A1 10/2007 Boock et al.
2007/0275193 A1 11/2007 DeSimone et al.
2007/0299385 A1 12/2007 Santini et al.
2007/0299409 A1 12/2007 Whitbourne et al.
2008/0001318 A1 1/2008 Schorzman et al.
2008/0021008 A1 1/2008 Pacetti et al.
2008/0027301 A1 1/2008 Ward et al.
2008/0031918 A1 2/2008 Lawin et al.
2008/0033269 A1 2/2008 Zhang
2008/0034972 A1 2/2008 Gough et al.
2008/0038307 A1 2/2008 Hoffmann
2008/0045824 A1 2/2008 Tapsak et al.
2008/0071027 A1 3/2008 Pacetti
2008/0076897 A1 3/2008 Kunzler et al.
2008/0081184 A1 4/2008 Kubo et al.
2008/0113207 A1 5/2008 Pacetti et al.
2008/0138497 A1 6/2008 Pacetti et al.
2008/0138498 A1 6/2008 Pacetti et al.
2008/0143014 A1 6/2008 Tang
2008/0187655 A1 8/2008 Markle et al.
2008/0188722 A1 8/2008 Markle et al.
2008/0188725 A1 8/2008 Markle et al.
2008/0210557 A1 9/2008 Heller et al.
2008/0213460 A1 9/2008 Benter et al.
2008/0305009 A1 12/2008 Gamsey et al.
2008/0305506 A1 12/2008 Suri
2008/0312397 A1 12/2008 Lai et al.
2009/0004243 A1 1/2009 Pacetti et al.
2009/0012205 A1 1/2009 Nakada et al.
2009/0018418 A1 1/2009 Markle et al.
2009/0018426 A1 1/2009 Markle et al.
2009/0030294 A1 1/2009 Petisce et al.
2009/0045055 A1 2/2009 Rhodes et al.
2009/0061528 A1 3/2009 Suri
2009/0081803 A1 3/2009 Gamsey et al.
2009/0177143 A1 7/2009 Markle et al.
2009/0247855 A1 10/2009 Boock et al.
2009/0247856 A1 10/2009 Boock et al.
2009/0264719 A1 10/2009 Markle et al.
2009/0287073 A1 11/2009 Boock et al.
2010/0076283 A1 3/2010 Simpson et al.
2010/0096259 A1 4/2010 Zhang et al.
2010/0280347 A1 11/2010 Shah et al.

FOREIGN PATENT DOCUMENTS

EP 0 127 958 12/1984
EP 0 291 130 11/1988
EP 0 313 951 5/1989
EP 0 320 109 6/1989
EP 0 353 328 2/1990
EP 0 362 145 4/1990
EP 0 390 390 10/1990
EP 0 396 788 11/1990
EP 0 535 898 4/1993
EP 0 563 795 10/1993
EP 0 817 809 B1 1/1998
EP 0 862 648 9/1998
EP 0 885 932 A2 12/1998
EP 1 153 571 11/2001
EP 1153571 11/2001
GB 1 442 303 7/1976

| | | |
|---|---|---|
| GB | 2149918 | 6/1985 |
| GB | 2209836 | 5/1989 |
| JP | 57156004 | 9/1982 |
| JP | 57156005 | 9/1982 |
| JP | 58163402 | 9/1983 |
| JP | 58163403 | 9/1983 |
| JP | 59029693 | 2/1984 |
| JP | 59049803 | 3/1984 |
| JP | 59049805 | 3/1984 |
| JP | 59059221 | 4/1984 |
| JP | 59087004 | 5/1984 |
| JP | 59-211459 | 11/1984 |
| JP | 59209608 | 11/1984 |
| JP | 59209609 | 11/1984 |
| JP | 59209610 | 11/1984 |
| JP | 60245623 | 12/1985 |
| JP | 61238319 | 10/1986 |
| JP | 62074406 | 4/1987 |
| JP | 62102815 | 5/1987 |
| JP | 62227423 | 10/1987 |
| JP | 63130661 | 6/1988 |
| JP | 01018404 | 1/1989 |
| JP | 01018405 | 1/1989 |
| JP | 05279447 | 10/1993 |
| JP | 07-083871 | 3/1995 |
| JP | 8196626 | 8/1996 |
| JP | 10-026601 | 1/1998 |
| JP | 2002055076 A | 2/2002 |
| WO | WO 89/02720 | 4/1989 |
| WO | WO 90/07575 | 7/1990 |
| WO | WO 92/13271 | 8/1992 |
| WO | WO 93/14185 | 7/1993 |
| WO | WO 93/14693 | 8/1993 |
| WO | WO 93/23744 | 11/1993 |
| WO | WO 94/08236 | 4/1994 |
| WO | WO 96/14026 | 5/1996 |
| WO | WO 96/25089 | 8/1996 |
| WO | WO 96/30431 | 10/1996 |
| WO | WO 97/01986 | 1/1997 |
| WO | WO 97/11067 | 3/1997 |
| WO | WO 98/30891 | 7/1998 |
| WO | WO 98/38906 | 9/1998 |
| WO | WO 99/56613 | 4/1999 |
| WO | WO 00/59373 | 10/2000 |
| WO | WO 00/074753 | 12/2000 |
| WO | WO 01/20019 A2 | 3/2001 |
| WO | WO 02/053764 | 7/2002 |
| WO | WO 02/089666 | 11/2002 |
| WO | WO 03/011131 | 2/2003 |
| WO | WO 2005/044088 | 5/2005 |
| WO | WO 2005/044088 A2 | 5/2005 |
| WO | WO 2005/045394 | 5/2005 |
| WO | WO 2006/018425 | 2/2006 |
| WO | WO 2007/114943 | 10/2007 |

OTHER PUBLICATIONS

Aalders et al. 1991. Development of a wearable glucose sensor; studies in healthy volunteers and in diabetic patients. The International Journal of Artificial Organs 14(2):102-108.
Abe et al. 1992. Characterization of glucose microsensors for intracellular measurements. Alan. Chem. 64(18):2160-2163.
Abel et al. 1984. Experience with an implantable glucose sensor as a prerequisite of an artifical beta cell, Biomed. Biochim. Acta 43(5):577-584.
Abel et al. 2002. Biosensors for in vivo glucose measurement: can we cross the experimental stage. Biosens Bioelectron 17:1059-1070.
Alcock & Turner. 1994. Continuous Analyte Monitoring to Aid Clinical Practice. IEEE Engineering in Med. & Biol. Mag. 13:319-325.
American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662-667.
Answers.com. "xenogenic." The American Heritage Stedman's Medical Dictionary. Houghton Mifflin Company, 2002. Answers. com Nov. 7, 2006 http://www. Answers.com/topic/xenogenic.
Atanasov et al. 1994. Biosensor for continuous glucose monitoring. Biotechnology and Bioengineering 43:262-266.
Atanasov et al. 1997. Implantation of a refillable glucose monitoring-telemetry device. Biosens Bioelectron 12:669-680.
Aussedat et al. 1997. A user-friendly method for calibrating a subcutaneous glucose sensor-based hypoglycaemic alarm. Biosensors & Bioelectronics 12(11):1061-1071.
Bailey et al. 2007. Reduction in hemoglobin A1c with real-time continuous glucose monitoring: results from a 12-week observational study. Diabetes Technology & Therapeutics 9(3):203-210.
Beach et al. 1999. Subminiature implantable potentiostat and modified commercial telemetry device for remote glucose monitoring. IEEE Transactions on Instrumentation and Measurement 48(6):1239-1245.
Bessman et al., Progress toward a glucose sensor for the artificial pancreas, Proceedings of a Workshop on Ion-Selective Microelectrodes, Jun. 4-5, 1973, Boston, MA, 189-197.
Biermann et al. 2008. How would patients behave if they were continually informed of their blood glucose levels? A simulation study using a "virtual" patient. Diab. Thechnol. & Therapeut., 10:178-187.
Bisenberger et al. 1995. A triple-step potential waveform at enzyme multisensors with thick-film gold electrodes for detection of glucose and sucrose. Sensors and Actuators, B 28:181-189.
Bland et al. 1990. A note on the use of the intraclass correlation coefficient in the evaluation of agreement between two methods of measurement. Comput. Biol. Med. 20(5):337-340.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics, 2(Suppl 1):S43-48.
Bode, B. W. 2000. Clinical utility of the continuous glucose monitoring system. Diabetes Technol Ther, 2(Suppl 1):S35-41.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bowman, L.; Meindl, J. D. 1986. The packaging of implantable integrated sensors. IEEE Trans Biomed Eng BME33(2):248-255.
Brauker et al. Jun. 27, 1996. Local Inflammatory Response Around Diffusion Chambers Containing Xenografts Transplantation 61(12):1671-1677.
Braunwald, 2008. Biomarkers in heart failure. *N. Engl. J. Med.*, 358: 2148-2159.
Bremer et al. 2001. Benchmark data from the literature for evaluation of new glucose sensing technologies. Diabetes Technology & Therapeutics 3(3):409-418.
Bruckel et al. 1989. In vivo measurement of subcutaneous glucose concentrations with an enzymatic glucose sensor and a wick method. Klin Wochenschr 67:491-495.
Cai et al. 2004. A wireless, remote query glucose biosensor based on a pH-sensitive polymer. Anal Chem 76(4):4038-4043.
Campanella et al. 1993. Biosensor for direct determination of glucose and lactate in undiluted biological fluids. Biosensors & Bioelectronics 8:307-314.
Candas et al (1994). "An adaptive plasma glucose controller basedon on a nonlinear insulin/glucose model." *IEEE Transactions on Biomedical Engineering*, 41(2): 116-124.
Cassidy et al., Apr. 1993. Novel electrochemical device for the detection of cholesterol or glucose, Analyst, 118:415-418.
Chase et al. 2001. Continuous subcutaneous glucose monitoring in children with type 1 diabetes. Pediatrics 107:222-226.
Chatterjee et al. 1997. Poly(ether Urethane) and poly(ether urethane urea) membranes with high $H_2S/CH_4$ selectivity, Journal of Membrane Science 135:99-106.
Ciba® Irgacure 2959 Photoinitiator Product Description, Ciba Specialty Chemicals Inc., Basel, Switzerland.
Claremont et al. 1986. Subcutaneous implantation of a ferrocene-mediated glucose sensor in pigs. Diabetologia 29:817-821.
Claremont et al. Jul. 1986. Potentially-impintable, ferrocene-mediated glucose sensor. J. Biomed. Eng. 8:272-274.

Clark et al., 1981. One-minute electrochemical enzymic assay for cholesterol in biological materials, Clin. Chem. 27(12):1978-1982.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.
Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529-536.
Csoregi et al., 1994. Design, characterization, and one-point in vivo calibration of a subcutaneously implanted glucose electrode. Anal Chem. 66(19):3131-3138.
Danielsson et al. 1988. Enzyme thermistors, Methods in Enzymology, 137:181-197.
Dassau et al., In silico evaluation platform for artifical pancreatic β-cell development-a dynamic simulator for closed loop control with hardware-in-the-loop, Diabetes Technology & Therapeutics, 11(3):1-8, 2009.
Davis et al. 1983. Bioelectrochemical fuel cell and sensor based on a quinoprotein, alcohol dehydrogenase. *Enzyme Microb. Technol.*, vol. 5, September, 383-388.
Direct 30/30® meter (Markwell Medical) (Catalog).
DuPont[1] Dimension AR® (Catalog), 1998.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El Degheidy et al. 1986. Optimization of an implantable coated wire glucose sensor. J. Biomed Eng. 8:121-129.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
Ei-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Anal. Bioanal. Chem. 373:758-761.
Fahy et al., An analysis: hyperglycemic intensive care patients need continuous glocuse monitoring—easier said than done, Journal of Diabetese Science and Technology, 2(2):201-204, Mar. 2008.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technol Ther 5(5):769-779.
Fischer et al. 1987. Assessment of subcutaneous glucose concentration: validation of the wick technique as a reference for implanted electrochemical sensors in normal and diabetic dogs, Diabetologia 30:940-945.
Fischer et al. 1989. Oxygen Tension at the Subcutaneous Implantation Site of Glucose Sensors. Biomed. Biochem 11/12:965-972.
Fischer et al. 1995. Hypoglycaemia-warning by means of subcutaneous electrochemical glucose sensors: an animal study, Horm. Metab. Rese. 27:53.
Freedman et al. 1991. Statistics, Second Edition, W.W. Norton & Company, p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diab. Thechnol. & Therapeut., 10:188-193.
Ganesan et al., Gold layer-based dual crosslinking procedure of glucose oxidase with ferrocene monocarboxylic acid provides a stable biosensor, Analytical Biochemistry 343:188-191, 2005.
Ganesh et al., Evaluation of the VIA@ blood chemistry monitor for glucose in healthy and diabetic volunteers, Journal of Diabetese Science and Technology, 2(2):182-193, Mar. 2008.
Gao et al. 1989. Determination of Interfacial parameters of cellulose acetate membrane materials by HPLC, *J. Liquid Chromatography*, VI. 12, n. 11, 2083-2092.
Garg et al. 2004. Improved Glucose Excursions Using an Implantable Real-Time continuous Glucose Sensor in Adults with Type I Diabetes. Diabetes Care 27:734-738.
Gerritsen et al. 1999. Performance of subcutaneously implanted glucose sensors for continuous monitoring. The Netherlands Journal of Medicine 54:167-179.
Gerritsen, M. 2000. Problems associated with subcutaneously implanted glucose sensors. Diabetes Care 23(2):143-145.
Gilligan et al. 1994. Evaluation of a subcutaneous glucose sensor out to 3 months in a dog model. Diabetes Care 17(8):882-887.
Godsland et al. 2001. Maximizing the Success Rate of Minimal Model Insulin Sensitivity Measurement in Humans: The Importance of Basal Glucose Levels. The Biochemical Society and the Medical Research Society, 1-9.
Gouda et al., Jul. 4, 2003. Thermal inactiviation of glucose oxidase, The Journal of Biological Chemistry, 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gross et al. 2000. Efficacy and reliability of the continuous glucose monitoring system. Diabetes Technology & Therapeutics, 2(Suppl 1):S19-26.
Gross et al. 2000. Performance evaluation of the MiniMed® continuous glucose monitoring system during patient home use. Diabetes Technology & Therapeutics 2(1):49-56.
Guerci et al., Clinical performance of CGMS in type 1 diabetic patents treated by continuous subcutaneous insulin infusion using insulin analogs, Diabetes Care, 26:582-589, 2003.
Guo et al., Modification of cellulose acetate ultrafiltration membrane by gamma ray radiation, Shuichuli Jishi Bianji Weiyuanhui, 23(6):315-318, 1998 (Abstract only).
Hall et al. 1998. Electrochemical oxidation of hydrogen peroxide at platinum electrodes. Part I: An adsorption-controlled mechanism. Electrochimica Acta, 43(5-6):579-588.
Hall et al. 1998. Electrochemical oxidation of hydrogen peroxide at platinum electrodes. Part II: Effect of potential. Electrochimica Acta 43(14-15):2015-2024.
Hall et al. 1999. Electrochemical oxidation of hydrogen peroxide at platinum electrodes. Part III: Effect of temperature. Electrochimica Acta, 44:2455-2462.
Hall et al. 1999. Electrochemical oxidation of hydrogen peroxide at platinum electrodes. Part IV: Phosphate buffer dependence. Electrochimica Acta, 44:4573-4582.
Hall et al. 2000. Electrochemical oxidation of hydrogen peroxide at platinum electrodes. Part V: Inhibition by chloride. Electrochimica Acta, 45:3573-3579.
Hamilton Syringe Selection Guide. 2006. Syringe Selection. www.hamiltoncompany.com.
Harrison et al. 1988. Characterization of perfluorosulfonic acid polymer coated enzyme electrodes and a miniaturized integrated potentiostat for glucose analysis in whole blood. Anal. Chem. 60:2002-2007.
Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes C.*
Heller, A. 2003. Plugging metal connectors into enzymes. Nat Biotechnol 21:631-2.

Hoel, Paul G. 1976. Elementary Statistics, Fourth Edition. John Wiley & Sons, Inc.. pp. 113-114.
Hrapovic et al. 2003. Picoamperometric detection of glucose at ultrasmall platinum-based biosensors: preparation and characterization. Anal Chem 75:3308-3315.
http://www.merriam-webster.com/dictionary, definition for "aberrant," Aug. 19, 2008, p. 1.
Huang et al. A 0.5mV passive telemetry IC for biomedical applications. Swiss Federal Institute of Technology. 4 pp.
Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.
Hunter et al. 2000. Minimally Invasive Glucose Sensor and Insulin Delivery System. MIT Home Automation and Healthcare Consortium. Progress Report No. 25.
Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.
Jensen et al. 1997. Fast wave forms for pulsed electrochemical detection of glucose by incorporation of reductive desorption of oxidation products. Analytical Chemistry 69(9):1776-1781.
Jeutter, D. C. 1982. A transcutaneous implanted battery recharging and biotelemeter power switching system. IEEE Trans Biomed Eng 29:314-321.
Johnson (1991). "Reproducible electrodeposition of biomolecules for the fabrication of miniature electroenzymatic biosensors," *Sensors and Actuators B*, 5:85-89.
Jovanovic, L. 2000. The role of continuous glucose monitoring in gestational diabetes mellitus. Diabetes Technology & Therapeutics, 2 Suppl 1, S67-71.
Kacaniklic May-Jun. 1994. Electroanalysis, 6(5-6):381-390.
Kamath et al. Calibration of a continuous glucose monitor: effect of glucose rate of change, Eighth Annual Diabetes Technology Meeting, Nov. 13-15, 2008, p. A88.
Kaufman. 2000. Role of the continuous glucose monitoring system in pediatric patients. Diabetes Technology & Therapeutics 2(1):S-49-S-52.
Kaufman et al. 2001. A pilot study of the continuous glucose monitoring system. Diabetes Care 24(12):2030-2034.
Keedy et al. 1991. Determination of urate in undiluted whole blood by enzyme electrode. *Biosensors & Bioelectronics*, 6: 491-499.
Kerner et al. 1988. A potentially implantable enzyme electrode for amperometric measurement of glucose, Horm Metab Res Suppl. 20:8-13.
Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.
Ko, Wen H. 1985. Implantable Sensors for Closed-Loop Prosthetic Systems, Futura Pub. Co., Inc., Mt. Kisco, NY, Chapter 15:197-210.
Kondo et al. 1982. A miniature glucose sensor, implantable in the blood stream. Diabetes Care. 5(3):218-221.
Koschinsky et al. 1988. New approach to technical and clinical evaluation of devices for self-monitoring of blood glucose. Diabetes Care 11(8): 619-619.
Koschinsky et al. 2001. Sensors for glucose monitoring: Technical and clinical aspects. Diabetes Metab. Res. Rev. 17:113-123.
Kost et al. 1985. Glucose-sensitive membranes containing glucose oxidase: activitiy, swelling, and permeability studies, Journal of Biomedical Materials Research 19:1117-1133.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Kraver et al. 2001. A mixed-signal sensor interface microinstrument. Sensors and Actuators A 91:266-277.
Kruger et al. 2000. Psychological motivation and patient education: A role for continuous glucose monitoring. Diabetes Technology & Therapeutics, 2(Suppl 1):S93-97.
Kulys et al., 1994. Carbon-paste biosensors array for long-term glucose measurement, Biosensors& Beioelectronics, 9:491-500.
Kunjan et al., Automated blood sampling and glocuse sensing in critical care settings, Journal of Diabetes Science and Technology 2(3):194-200, Mar. 2008.
Kurtz et al. 2005. Recommendations for blood pressure measurement in humans and experimental animals, Part 2: Blood pressure measurement in experimental animals, A statement for professionals from the subcommittee of professional and public education of.
Ladd et al., Structure Determination by X-ray Crystallography, 3rd ed. Plenum, 1996, Ch. 1, pp. xxi-xxiv and 1-58.
Lehmann et al. May 1994. Retrospective valication of a physiological model of glucose-iunsulin interaaction in tyhpe 1 diabetes mellitus, Med. Eng. Phys. 16:193-202.
Lerner et al. 1984. An implantable electrochemical glucose sensor. Ann. N. Y. Acad. Sci. 428:263-278.
Lewandowski et al. 1988. Evaluation of a miniature blood glucose sensor. Trans Am Soc Artif Intern Organs 34:255-258.
Linke et al. 1994. Amperometric biosensor for in vivo glucose sensing based on glucose oxidase immobilized in a redox hydrogel. Biosensors & Bioelectronics 9:151-158.
Lowe, 1984. Biosensors, Trends in Biotechnology, 2(3):59-65.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Lyandres et al. (2008). Progress toward an in vivo surface-enhanced raman spectroscopy glucose sensor. *Diabetes Technology & Therapeutics*, 10(4): 257-265.
Makale et al. 2003. Tissue window chamber system for validation of implanted oxygen sensors. Am. J. Physiol. Heart Circ. Physiol. 284:H2288-2294.
Malin et al. 1999. Noninvasive Prediction of Glucose by Near-Infrared Diffuse Reflectance Spectroscopy. Clinical Chemistry 45:9, 1651-1658.
Maran et al. 2002. Continuous subcutaneous glucose monitoring in diabetic patients: A multicenter analysis. Diabetes Care 25(2):347-352.
March, W. F. 2002. Dealing with the delay. Diabetes Technol Ther 4(1):49-50.
Marena et al. 1993. The artifical endocrine pancreas in clinical practice and research. Panminerva Medica 35(2):67-74.
Mascini et al. 1989. Glucose electrochemical probe with extended linearity for whole blood. *J Pharm Biomed Anal 7*(12): 1507-1512.
Mastrototaro, J. J. 2000. The MiniMed continuous glucose monitoring system. Diabetes Technol Ther 2(Suppl 1):S13-8.
Mastrototaro et al. 2003. Reproducibility of the continuous glucose monitoring system matches previous reports and the intended use of the product. Diabetes Care 26:256; author reply p. 257.
Matsumoto et al. 1998. A micro-planar amperometeric glucose sensor unsusceptible to interference species. Sensors and Actuators B 49:68-72.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diab. Thechnol. & Therapeut., 10:149-159.
McCartney et al. 2001. Near-infrared fluorescence lifetime assay for serum glucose based on allophycocyanin-labeled concanavalin A. Anal Biochem 292:216-221.
McGrath et al. 1995. The use of differential measurements with a glucose biosensor for interference compensation during glucose determinations by flow injection analysis. Biosens Bioelectron 10:937-943.
Memoli et al. 2002. A comparison between different immobilised glucoseoxidase-based electrodes. J Pharm Biomed Anal 29:1045-1052.
Merriam-Webster Online Dictionary. Definition of "acceleration". http://www.merriam-webster.com/dictionary/Acceleration Jan. 11, 2010.
Merriam-Webster Online Dictionary. Definition of "system". http://www.merriam-webster.com/dictionary/System Jan. 11, 2010.

Merriam-Webster Online Dictionary. The term "nominal." http://www.m-w.com/dictionary/nominal.
Meyerhoff et al. 1992. On line continuous monitoring of subcutaneous tissue glucose in men by combining portable glucosensor with microdialysis. Diabetologia 35:1087-1092.
Moatti-Sirat et al. 1992. Evaluating in vitro and in vivo the interference of ascorbate and acetaminophen on glucose detection by a needle-type glucose sensor, Biosensors & Bioelectronics 7:345-352.
Moatti-Sirat et al., Reduction of acetaminophen interference in glucose sensors by a composite Nafion membrane: demonstration in rats and man, Diabetologia 37(6):610-616, Jun. 1994.
Morff et al. 1990. Microfabrication of reproducible, economical, electroenzymatic glucose sensors, Annual International Conference of the IEEE Engineering in Medicine and Biology Society, 12(2):0483-0484.
Mosbach et al. 1975. Determination of heat changes in the proximity of immobilized enzymes with an enzyme termistor and its use for the assay of metobolites, Biochim. Biophys. Acta. (Enzymology), 403:256-265.
Motonaka et al. 1993. Determination of cholesteral and cholesteral ester with novel enzyme microsensors, Anal. Chem. 65:3258-3261.
Muslu. 1991. Trickling filter performance. Apllied Biochemistry and Biotechnology 37:211-224.
Nafion® 117 Solution Product Description, Product No. 70160, Sigma-Aldrich Corp., St. Louis, MO.
Ohara et al. 1994. "Wired" enzyme electrodes for amperometric determination of glucose or lactate in the presence of interfering substances. Anal Chem 66:2451-2457.
Okuda et al. 1971. Mutarotase effect on micro determinations of D-glucose and its anomers with β-D-glucose oxidase. Anal Biochem 43:312-315.
Oxford English Dictionary Online. Definition of "impending". http://www.askoxford.com/results/?view=dev dict&field-12668446 Impending&branch= Jan. 11, 2010.
Palmisano et al. 2000. Simultaneous monitoring of glucose and lactate by an interference and cross-talk free dual electrode amperometric biosensor based on electropolymerized thin films. Biosensors & Bioelectronics 15:531-539.
Park et al. 2002. Gas separation properties of polysiloxane/polyether mixed soft segment urethane urea membranes, *J. Membrane Science*, 204: 257-269.
Patel et al. 2003. Amperometric glucose sensors based on ferrocene containing polymeric electron transfer systems—a preliminary report. Biosens Bioelectron 18:1073-6.
Peacock et al. 2008. Cardiac troponin and outcome in acute heart failure. N. Engl. J. Med., 358: 2117-2126.
Pfeiffer et al. 1992. On line continuous monitoring of subcutaneous tissue glucose is feasible by combining portable glucosensor with microdialysis. Horm. Metab. Res. 25:121-124.
Pfeiffer, E.F. 1990. The glucose sensor: the missing link in diabetes therapy, Horm Metab Res Suppl. 24:154-164.
Pichert et al. 2000. Issues for the coming age of continuous glucose monitoring Diabetes Educ 26(6):969-980.
Pickup et al. 1989. Potentially-implantable, amperometric glucose sensors with mediated electron transfer: improving the operating stability. Biosensors 4:109-119.
Pickup et al. 1993. Developing glucose sensors for in vivo use. Elsevier Science Publishers Ltd (UK), TIBTECH vol. 11: 285-291.
Pinner et al., Cross-linking of cellulose acetate by ionizing radiation, Nature, vol. 184, 1303-1304, Oct. 24, 1959.
Pitzer et al. 2001. Detection of hypoglycemia with the GlucoWatch biographer. Diabetes Care 24(5):881-885.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode, Electrochimica Acta 26(6):725-729.
Quinn et al. 1995. Kinetics of glucose delivery to subcutaneous tissue in rats measured with 0.3-mm amperometric microsensors. The American Physiological Society E155-E161.
Rabah et al., 1991. Electrochemical wear of graphite anodes during electrolysis of brine, Carbon, 29(2):165-171.
Reach et al. 1986. A Method for Evaluating in vivo the Functional Characteristics of Glucose Sensors. Biosensors 2:211-220.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000;2:49-56. Diabetes Technology & Therapeutics 3(1):129-130.
Rebrin et al. 1992. Subcutaenous glucose monitoring by means of electrochemical sensors: fiction or reality? J. Biomed. Eng. 14:33-40.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rigla et al. 2008. Real-time continuous glucose monitoring together with telemedical assitance improves glycemic control and glucose stability in pump-treated patients. Diab. Thechnol. & Therapeut., 10:194-199.
Rivers et al., Central venous oxygen saturation monitoring in the critically ill patient, Current Opinion in Critical Care, 7:204-211, 2001.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Salardi et al. 2002. The glucose area under the profiles obtained with continuous glucose monitoring system relationships with HbA1c in pediatric type 1 diabetic patients. Diabetes Care 25(10):1840-1844.
San Diego Plastics, Inc. 2009. Polyethylene Data Sheet, http://www.sdplastics.com/polyeth.html.
Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.
Sansen et al. 1990. A smart sensor for the voltammetric measurement of oxygen or glucose concentrations. Sensors and Actuators B 1:298-302.
Schmidt et al. 1993. Glucose concentration in subcutaneous extracellular space. Diabetes Care 16(5):695-700.
Schmidtke et al., Measurement and modeling of the transient difference between blood and subcutaneous glucose concentrations in the rat after injection of insulin. *Proc Natl Acad Sci U S A* 1998, 95, 294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Service et al. 1970. Mean amplitude of glycemic excursions, a measure of diabetic instability. Diabetes, 19: 644-655.
Service et al. 1987. Measurements of glucose control. Diabetes Care, 10: 225-237.
Service, R. F. 2002. Can sensors make a home in the body? Science 297:962-3.
Sharkawy et al. 1996. Engineering the tissue which encapsulates subcutaneous implants. I. Diffusion properties, J Biomed Mater Res, 37:401-412.
Shichiri et al. 1982. Wearable artificial endocrine pancrease with needle-type glucose sensor. Lancet 2:1129-1131.
Shichiri et al. 1983. Glycaemic Control in Pancreatectomized Dogs with a Wearable Artificial Endocrine Pancreas. Diabetologia 24:179-184.
Skyler, J. S. 2000. The economic burden of diabetes and the benefits of improved glycemic control: The potential role of a continuous glucose monitoring system. Diabetes Technology & Therapeutics 2 Suppl 1:S7-12.
Slater-Maclean et al. 2008. Accuracy of glycemic measurements in the critically ill. Diab. Thechnol. & Therapeut., 10:169-177.

Sriyudthsak et al. 1996. Enzyme-epoxy membrane based glucose analyzing system and medical applications. Biosens Bioelectron 11:735-742.
Steil et al. 2003. Determination of plasma glucose during rapid glucose excursions with a subcutaneous glucose sensor. Diabetes Technology & Therapeutics 5(1):27-31.
Stern et al., 1957. Electrochemical polarization: 1. A theoretical analysis of the shape of polarization curves, Journal of the Electrochemical Society, 104(1):56-63.
Sumino T. et al. 1998. Preliminary study of continuous glucose monitoring with a microdialysis technique. Proceedings of the IEEE, 20(4):1775-1778.
Tanenberg et al. 2000. Continuous glucose monitoring system: A new approach to the diagnosis of diabetic gastroparesis. Diabetes Technology & Therapeutics, 2 Suppl 1:S73-80.
Tatsuma et al. 1991. Oxidase/peroxidase bilayer-modified electrodes as sensors for lactate, pyruvate, cholesteral and uric acid, Analytica Chimica Acta, 242:85-89.
Thome et al. 1995.—Abstract—Can the decrease in subcutaneous glucose concentration precede the decrease in blood glucose level? Proposition for a push-pull kinetics hypothesis, Horm. Metab. Res. 27:53.
Thomé-Duret et al. 1996. Modification of the sensitivity of glucose sensor implanted into subcutaneous tissue. Diabetes Metabolism, 22:174-178.
Thomé-Duret et al. 1998. Continuous glucose monitoring in the free-moving rat. Metabolism, 47:799-803.
Tierney et al. 2000. Effect of acetaminophen on the accuracy of glucose measurements obtained with the GlucoWatch biographer. Diabetes Technol Ther 2:199-207.
Tierney et al. 2000. The GlucoWatch® biographer: A frequent, automatic and noninvasive glucose monitor. Ann. Med. 32:632-641.
Torjman et al., Glucose monitoring in acute care: technologies on the horizon, Journal of Deabetes Science and Technology, 2(2):178-181, Mar. 2008.
Trecroci, D. 2002. A Glimpse into the Future—Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner et al. 1984. Carbon Monoxide: Acceptor Oxidoreductase from *Pseudomonas thermocarboxydovorans* Strain C2 and its use in a Carbon Monoxide Sensor. Analytica Chimica Acta, 163: 161-174.
Unger et al. 2004. Glucose control in the hospitalized patient. Emerg Med 36(9):12-18.
Updike et al. 1967. The enzyme electrode. Nature, 214:986-988.
Updike et al. 1988. Laboratory Evaluation of New Reusable Blood Glucose Sensor. Diabetes Care, 11:801-807.
Updike et al. 1994. Enzymatic glucose sensor: Improved long-term performance in vitro and in vivo. ASAIO Journal, 40(2):157-163.
Updike et al. 2000. A subcutaneous glucose sensor with improved longevity, dynamic range, and stability of calibration. Diabetes Care 23(2):208-214.
Utah Medical Products Inc., Blood Pressure Tranducers product specifications. 6 pp. 2003-2006, 2003.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.
Ward et al. 2000. Rise in background current over time in a subcutaneous glucose sensor in the rabbit: Relevance to calibration and accuracy. Biosensors & Bioelectronics, 15:53-61.
Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50-55.
Wilkins et al. 1995. Integrated implantable device for long-term glucose monitoring. Biosens. Bioelectron 10:485-494.
Wilson et al. 2000. Enzyme-based biosensors for in vivo measurements. Chem. Rev., 100:2693-2704.
Wood, W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)—modified myoglobin, Electrochemistry Communications 1 (1999) 603-611.
Yamasaki, Yoshimitsu. Sep. 1984. The development of a needle-type glucose sensor for wearable artificial endocrine pancreas. Medical Journal of Osaka University 35(1-2):25-34.
Yamasaki et al. 1989. Direct measurement of whole blood glucose by a needle-type sensor. Clinica Chimica Acta. 93:93-98.
Yang et al (1996). "A glucose biosensor based on an oxygen electrode: In-vitro performances in a model buffer solution and in blood plasma," Biomedical Instrumentation & Technology, 30:55-61.
Yang et al. 1998. Development of needle-type glucose sensor with high selectivity. Science and Actuators B 46:249-256.
Yang, et al. 2004. A Comparison of Physical Properties and Fuel Cell Performance of Nafion and Zirconium Phosphate/Nafion Composite Membranes. Journal of Membrane Science 237:145-161.
Ye et al. 1993. High Current Density 'Wired' Quinoprotein Glucose Dehydrogenase Electrode. Anal. Chem. 65:238-241.
Zamzow et al. Development and evaluation of a wearable blood glucose monitor. pp. M588-M591, 1990.
Zethelius et al. 2008. Use of multiple biomarkers to improve the prediction of death from cardiovascular causes. N. Engl. J. Med., 358: 2107-2116.
Zhang et al (1993). Electrochemical oxidation of $H_2O_2$ on Pt and Pt + Ir electrodes in physiological buffer and its applicability to $H_2O_2$-based biosensors. *J. Electroanal. Chem.*, 345:253-271.
Zhang et al. 1993. In vitro and in vivo evaluation of oxygen effects on a glucose oxidase based implantable glucose sensor. Analytica Chimica Acta, 281:513-520.
Zhang et al. 1994. Elimination of the acetaminophen interference in an implantable glucose sensor. Analytical Chemistry 66(7):1183-1188.
Zhu et al. (1994). "Fabrication and characterization of glucose sensors based on a microarray $H_2O_2$ electrode." *Biosensors & Bioelectronics*, 9: 295-300.
Zhu et al. 2002. Planar amperometric glucose sensor based on glucose oxidase immobilized by chitosan film on prussian blue layer. Sensors, 2:127-136.
Office Action dated Sep. 24, 2003 in U.S. Appl. No. 09/916,711.
Office Action dated Feb. 11, 2004 in U.S. Appl. No. 09/916,711.
Office Action dated Jul. 23, 2004 in U.S. Appl. No. 09/916,711.
Office Action dated Dec. 23, 2004 in U.S. Appl. No. 09/916,711.
Office Action dated Jul. 1, 2005 in U.S. Appl. No. 09/916,711.
Office Action dated Feb. 14, 2006 in U.S. Appl. No. 09/916,711.
Office Action dated Sep. 5, 2006 in U.S. Appl. No. 09/916,711.
Office Action dated Feb. 17, 2004 in U.S. Appl. No. 10/153,356.
Office Action dated Aug. 12, 2004 in U.S. Appl. No. 10/153,356.
Office Action dated Mar. 15, 2005 in U.S. Appl. No. 10/153,356.
Office Action dated Oct. 6, 2005 in U.S. Appl. No. 10/153,356.
Office Action dated Mar. 10, 2006 in U.S. Appl. No. 10/153,356.
Office Action dated Aug. 29, 2006 in U.S. Appl. No. 10/153,356.
Office Action dated Mar. 7, 2007 in U.S. Appl. No. 10/153,356.

Office Action dated Jul. 23, 2009 in U.S. Appl. No. 11/404,481.
Office Action dated Dec. 10, 2008 in U.S. Appl. No. 11/280,672.
Office Action dated Jun. 2, 2009 in U.S. Appl. No. 11/280,672.
Office Action dated Oct. 29, 2009 in U.S. Appl. No. 11/280,672.
Office Action dated Sep. 12, 2008 in U.S. Appl. No. 10/991,353.
Office Action dated Mar. 4, 2009 in U.S. Appl. No. 10/991,353.
Office Action dated Jul. 31, 2009 in U.S. Appl. No. 10/991,353.
Office Action dated Jan. 22, 2009 in U.S. Appl. No. 11/692,154.
Office Action dated Jul. 8, 2009 in U.S. Appl. No. 11/692,154.
Office Action dated Jul. 30, 2009 in U.S. Appl. No. 10/838,658.
Office Action dated Dec. 24, 2008 in U.S. Appl. No. 10/885,476.
Office Action dated Jun. 23, 2009 in U.S. Appl. No. 10/885,476.
Office Action dated May 5, 2008 in U.S. Appl. No. 11/077,713.
Office Action dated Feb. 10, 2009 in U.S. Appl. No. 11/077,713.
Office Action dated Sep. 2, 2009 in U.S. Appl. No. 11/077,713.
Office Action dated Jun. 27, 2008 in U.S. Appl. No. 11/077,693.
Office Action dated Dec. 26, 2008 in U.S. Appl. No. 11/077,693.
Office Action dated Sep. 4, 2009 in U.S. Appl. No. 11/077,693.
Office Action dated Jan. 10, 2008 in U.S. Appl. No. 11/077,714.
Office Action dated Jun. 22, 2009 in U.S. Appl. No. 11/360,262.
Office Action dated Jul. 26, 2007 in U.S. Appl. No. 11/411,656.
Office Action dated Jun. 26, 2008 in U.S. Appl. No. 11/335,879.
Office Action dated Jan. 13, 2009 in U.S. Appl. No. 11/335,879.
Office Action dated Jun. 16, 2009 in U.S. Appl. No. 11/335,879.
Dixon, et al. 2002. Characterization in vitro and in vivo of the oxygen dependence of an enzyme/polymer biosensor for monitoring brain glucose. *Journal of Neuroscience Methods*, 119:135-142.
Gilligan, B. C.; Shults, M.; Rhodes, R. K.; Jacobs, P. G.; Brauker, J. H.; Pintar, T. J.; Updike, S. J. Feasibility of continuo long-term glucose monitoring from a subcutaneous glucose sensor in humans. Diabetes Technol Ther 2004, 6, 378-386.
Heller, A. Implanted electrochemical glucose sensors for the management of diabetes. Annu Rev Biomed Eng 1999, 1, 153-175.
Hitchman, M. L. 1978. "Measurement of Dissolved Oxygen." in Elving, et al. (Eds.). Chemical Analysis, vol. 49, Chap. 3, pp. 34-49, 59-123. New York: John Wiley & Sons.
Kang, S. K.; Jeong, R. A.; Park, S.; Chung, T. D.; Park, S.; Kim, H. C. In vitro and short-term in vivo characteristics of a Kel-F thin film modified glucose sensor. Anal Sci 2003, 19, 1481-1486.
Leypoldt, et al. 1984. Model of a two-substrate enzyme electrode for glucose. *Anal. Chem.*, 56:2896-2904.
Mancy, et al. 1962. A galvanic cell oxygen analyzer. *Journal of Electroanalytical Chemistry*, 4:65-92.
Matsumoto, et al. A long-term lifetime amperometric glucose sensor with a perfluorocarbon polymer coating. Biosens Bioelectron 2001, 16, 271-276.
Myler, et al. Ultra-thin-polysiloxane-film-composite membranes for the optimisation of amperometric oxidase enzyme electrodes. Biosens Bioelectron 2002, 17, 35-43.
Quinn, C. A.; Connor, R. E.; Heller, A. Biocompatible, glucose-permeable hydrogel for in situ coating of implantable biosensors. Biomaterials 1997, 18, 1665-1670.
Rhodes, et al. 1994. Prediction of pocket-portable and implantable glucose enzyme electrode performance from combined species permeability and digital simulation analysis. *Analytical Chemistry*, 66(9):1520-1529.
Schuler, R.; Wittkampf, M.; Chemniti , G. C. Modified gas-permeable silicone rubber membranes for covalent immobilisation of enzymes and their use in biosensor development. Analyst 1999, 124, 1181-1184.
Thomë-Duret, et al. 1996. Modification of the sensitivity of glucose sensor implanted into subcutaneous tissue. *Diabetes Metabolism*, 22:174-178.
Updike, et al. 1982. Implanting the glucose enzyme electrode: Problems, progress, and alternative solutions. *Diabetes Care*, 5(3):207-212.
Ward et al. 2002. A new amperometric glucose microsensor: In vitro and short-term in vivo evaluation. *Biosensors & Bioelectronics*, 17:181-189.
Wientjes, K. J. C. Development of a glucose sensor for diabetic patients. 2000.
Wilkins, E.; Atanasov, P. Glucose monitoring: state of the art and future possibilities. Med Eng Phys 1995, 18, 273-288.
Wilson, et al. 1992. Progress toward the development of an implantable sensor for glucose. *Clin. Chem.*, 38(9):1613-1617.
Wu, et al. 1999. In situ electrochemical oxygen generation with an immunoisolation device. *Ann. N.Y. Acad. Sci.*, 875:105-125.
U.S. Appl. No. 09/447,227, filed Nov. 22, 1999.
U.S. Appl. No. 10/838,658, filed May 3, 2004.
International Search Report for corresponding PCT application No. PCT/US04/23454, mailed on Oct. 19, 2005.
Written Opinion of International Search Report for corresponding PCT application No. PCT/US04/23454, mailed on Oct. 19, 2005.
U.S. Appl. No. 11/055,779, filed Feb. 9, 2005.
Asberg et al. 2003. Hydrogels of a Conducting Conjugated Polymer as 3-D Enzyme Electrode. Biosensors Bioelectronics. pp. 199-207.
Bindra et al. 1989. Pulsed amperometric detection of glucose in biological fluids at a surface-modified gold electrode. Anal Chem 61:2566-2570.
Bott, A. W. 1997. A Comparison of Cyclic Voltammetry and Cyclic Staircase Voltammetry Current Separations 16:1, 23-26.
Brauker et al. 1995. Neovascularization of synthetic membranes directed by membrane Microarchitecture. J. Biomed Mater Res 29:1517-1524.
Brauker et al. 1998. Sustained expression of high levels of human factor IX from human cells implanted within an immunoisolation device into athymic rodents. Hum Gene Ther 9:879-888.
Brauker et al. 2001. Unraveling Mysteries at the Biointerface: Molecular Mediator of Inhibition of Blood vessel Formation in the Foreign Body Capsule Revealed. Surfacts Biomaterials 6. 1;5.
Brunner et al. 1998. Validation of home blood glucose meters with respect to clinical and analytical approaches. Diabetes Care 21(4):585-590.
Cellulose Acetate Product Description, Product No. 419028, Sigma-Aldrich Corp., St. Louis, MO. 2005.
Chen et al. 2006. A noninterference polypyrrole glucose biosensor. Biosensors and Bioelectronics 22:639-643.
Dai et al. 1999. Hydrogel Membranes with Mesh Size Asymmetry Based on the Gradient Crosslink of Poly(vinyl alcohol). Journal of Membrane Science 156:67-79.
D'Arrigo et al. 2003. Porous-Si based bioreactors for glucose monitoring and drugs production. Proc. of SPIE 4982:178-184.
Deutsch et al., "Time series analysis and control of blood glucose levels in diabetic patients". Computer Methods and Programs in Biomedicine 41 (1994) 167-182.
Geller et al. 1997. Use of an immunoisolation device for cell transplantation and tumor immunotherapy. Ann NY Acad Sci 831:438-451.
Gerritsen et al. 2001. Influence of inflammatory cells and serum on the performance of implantable glucose sensors. J Biomed Mater Res 54:69-75.
Gregg et al. 1990. Cross-Linked Redox Gels Containing Glucose Oxidase for Amperometric Biosensor Applications. Anal. Chem. 62:258-263.
Johnson, R.C. et al., Abstract: Neovascularization of cell transplantation devices: Role of membrane architecture and encapsulated tissue, *Abstracts of Papers, Am. Chem. Soc.*, 1997, 214:2 P 305-PMSE.
Kargol et al. 2001. Studies on the structural properties of porous membranes: measurement of linear dimensions of solutes. Biophys Chem 91:263-271.
Karube et al. 1993. Microbiosensors for acetylcholine and glucose. Biosensors & Bioelectronics 8:219-228.
Kiechle, F.L. 2001. The impact of continuous glucose monitoring on hospital point-of-care testing programs. Diabetes Technol Ther 3:647-649.
Klueh et al. 2007. Inflammation and glucose sensors: use of dexamethasone to extend glucose sensor function and life span in vivo. Journal of Diabetes Science and Technology 1(4):496-504.
Kunzler et al. 1993. Hydrogels based on hydrophilic side chain siloxanes. Poly Mat Sci and Eng 69:226-227.
Kunzler et al. Aug. 21, 1995. Contact lens materials. Chemistry & Industry. 651-655.
Lee et al. 1999. Effects of pore size, void volume, and pore connectivity on tissue responses. Society for Biomaterials 25th Annual Meeting, 171.

Loffler et al. 1995. Separation and determination of traces of ammonia in air by means of chromatomembrane cells. Fresenius J Anal Chem 352:613-614.
Lyman D. 1960. Polyurethanes. I. The Solution Polymerization of Diisocyanates with Ethylene Glycol. J. Polymer Sci XLV:45:49.
Madaras et al. 1996. Microfabricated amperometric creatine and creatinine biosensors. Analytica Chimica Acta 319:335-345.
Miller, A. 1988. Human monocyte/macrophage activation and interleukin 1 generation by biomedical polymers. J Biomed Mater Res 23:713-731.
Miller et al. 1989. In vitro stimulation of fibroblast activity by factors generated from human monocytes activated by biomedical polymers. Journal of J Biomed Mater Res 23:911-930.
Miller et al. 1989. Generation of IL1-like activity in response to biomedical polymer implants: a comparison of in vitro and in vivo models. J Biomed Mater Res 23:1007-1026.
Moussy et al. 2000. Biomaterials community examines biosensor biocompatibility Diabetes Technol Ther 2:473-477.
Mowery et al. 2000. Preparation and characterization of hydrophobic polymeric films that are thromboresistant via nitric oxide release. Biomaterials 21:9-21.
Nakayama et al. 1992. Surface fixation of hydrogels: heparin and glucose oxidase hydrogelated surfaces. ASAIO Journal M421-M424.
Nam et al. 2000. A novel fabrication method of macroporous biodegradable polymer scaffolds using gas foaming salt as a porogen additive. J Biomed Mater Res 53:1-7.
Panetti 2002. Differential effects of sphingosine 1-phosphate and lysophosphatidic acid on endothelial cells. Biochimica et Biophysica Acta 1582:190-196.
Phillips and Smith. 1988. Bromedical Applications of Polyurethanes: Implications of Failure Mechanisms. J. Biomat. Appl. 3:202-227.
Pickup et al. 1988. Progress towards in vivo glucose sensing with a ferrocene-mediated amperometric enzyme electrode. 34-36.
Pineda et al. 1996. Bone regeneration with resorbable polymeric membranes. III. Effect of poly(L-lactide) membrane pore size on the bone healing process in large defects. J. Biomedical Materials Research 31:385-394.
Ratner, B.D. 2002. Reducing capsular thickness and enhancing angiogenesis around implant drug release systems. J Control Release 78:211-218.
Sachlos et al. 2003. Making Tissue Engineering Scaffolds Work. Review on the Application of Sold Freeform Fabrication Technology to the Production of Tissue Engineering Scaffolds. European Cells and Materials 5:29-40.
Sanders et al. 2003. Fibrous Encapsulation of Single Polymer Microfibers Depends on their Vertical Dimension in subcutaneous Tissue Polymer Microfibers pp. 1181-1187.
Selam, J. L. 1997. Management of diabetes with glucose sensors and implantable insulin pumps. From the dream of the 60s to the realities of the 90s. ASAIO J, 43:137-142.
Sieminski et al. 2000. Biomaterial-microvasculature interactions. Biomaterials 21:2233-2241.
Sternberg et al. 1988. Covalent enzyme coupling on cellulose acetate membranes for glucose sensor development. Anal. Chem. 69:2781-2786.
Stokes. 1988. Polyether Polyurethanes: Biostable or Not? J. Biomat. Appl. 3:228-259.
Suh et al. 2002. Behavior of fibroblasts on a porous hyaluronic acid incorporated collagen matrix. Yonsei Medical Journal 43(2):193-202.
Tang et al. 1993. Fibrin(ogen) mediates acute inflammatory responses to biomaterials. J Exp Med 178:2147-2156.
Tang et al. 1995. Inflammatory responses to biomaterials. Am J Clin Pathol 103:466-471.
Tang et al. 1996. Molecular determinants of acute inflammatory responses to biomaterials. J Clin Invest 97:1329-1334.
Tang et al. 1998. Mast cells mediate acute inflammatory responses to implanted biomaterials. Proc Natl Acad Sci U S A 95:8841-8846.
Tibell et al. 2001. Survival of macroencapsulated allogeneic parathyroid tissue one year after transplantation in nonimmunosuppressed humans. Cell Transplant 10:591-9.
Turner, A.P.F. 1988. Amperometric biosensor based on mediator-modified electrodes. Methods in Enzymology 137:90-103.
Wade Jr., L.G. Organic Chemistry, Chapter 17, Reactions of Aromatic Compounds pp. 762-763, 1987.
Office Action dated Aug. 15, 2001 in U.S. Appl. No. 09/447,227.
Office Action dated Jan. 17, 2002 in U.S. Appl. No. 09/447,227.
Office Action dated Jul. 15, 2002 in U.S. Appl. No. 09/447,227.
Office Action dated Jan. 16, 2003 in U.S. Appl. No. 09/447,227.
Office Action dated Jul. 9, 2003 in U.S. Appl. No. 09/447,227.
Office Action dated Nov. 28, 2003 in U.S. Appl. No. 09/447,227.
Office Action dated Sep. 22, 2005 in U.S. Appl. No. 09/447,227.
Office Action dated Apr. 4, 2006 in U.S. Appl. No. 09/447,227.
Office Action dated Aug. 1, 2006 in U.S. Appl. No. 09/447,227.
Office Action dated Mar. 9, 2007 in U.S. Appl. No. 09/447,227.
Office Action dated Jul. 17, 2007 in U.S. Appl. No. 09/447,227.
Office Action dated Jan. 23, 2008 in U.S. Appl. No. 09/447,227.
Office Action dated Jun. 12, 2008 in U.S. Appl. No. 09/447,227.
Office Action dated Dec. 11, 2008 in U.S. Appl. No. 09/447,227.
Office Action dated May 26, 2009 in U.S. Appl. No. 09/447,227.
Office Action dated Dec. 8, 2009 in U.S. Appl. No. 09/447,227.
Office Action dated Jan. 14, 2010 in U.S. Appl. No. 09/447,227.
Office Action dated Jan. 29, 2010 in U.S. Appl. No. 11/404,481.
Office Action dated Mar. 11, 2010 in U.S. Appl. No. 11/280,672.
Office Action dated Feb. 19, 2010 in U.S. Appl. No. 11/675,063.
Office Action dated Jan. 13, 2010 in U.S. Appl. No. 12/139,305.
Office Action dated Jan. 14, 2010 in U.S. Appl. No. 10/991,353.
Office Action dated Dec. 15, 2008 in U.S. Appl. No. 10/838,658.
Office Action dated Mar. 30, 2010 in U.S. Appl. No. 10/838,658.
Office Action dated Jan. 20, 2010 in U.S. Appl. No. 11/077,713.
Office Action dated Apr. 14, 2010 in U.S. Appl. No. 11/360,262.
Direct 30/30® Blood Glucose Sensor, (Markwell Medical) Catalog, © 1990, ELCO Diagnostics Company.
Huang et al., "A 0.5mW Passive Telemetry IC for Biomedical Applications," Proceedings of the 23rd European Solid-State Circuits Conference (ESSCIRC '97), pp. 172-175, Sep. 1997, Southampton, UK.
Merriam-Webster Online Dictionary. Definition of "nominal." http://www.m-w.com/dictionary/nominal Apr. 23, 2007.
Nafion® 117 Solution Product Description, Product No. 70160, Sigma-Aldrich Corp., St. Louis, MO. Apr. 7, 2005.
Japanese Office Action dated Jun. 1, 2010 in JP App. No. 2006-521208.
Official Communication dated May 18, 2010 in European App. No. 04778806.2.
Armour et al. Dec. 1990. Application of Chronic Intravascular Blood Glucose Sensor in Dogs. Diabetes 39:1519-1526.
Bellucci et al. Jan. 1986. Electrochemical behaviour of graphite-epoxy composite materials (GECM) in aqueous salt solutions, Journal of Applied Electrochemistry, 16(1):15-22.
Bindra et al. 1991. Design and In Vitro Studies of a Needle-Type Glucose Senso for Subcutaneous Monitoring. Anal. Chem 63:1692-96.
Bobbioni-Harsch et al. 1993. Lifespan of subcutaneous glucose sensors and their performances during dynamic glycaemia changes in rats, J. Biomed. Eng. 15:457-463.
Brooks et al. "Development of an on-line glucose sensor for fermentation monitoring," Biosensors, 3:45-56 (1987/88).
Cass et al. "Ferrocene-mediated enzyme electrodes for amperometric determination of glucose," Anal. Chem., 36:667-71 (1984).
Davies, et al. 1992. Polymer membranes in clinical sensor applications. I. An overview of membrane function, Biomaterials, 13(14):971-978.
Heller, "Electrical wiring of redox enzymes,"*Acc. Chem. Res.*, 23:128-134 (1990).
Heller, A. 1992. Electrical Connection of Enzyme Redox Centers to Electrodes. J. Phys. Chem. 96:3579-3587.
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Johnson et al. 1992. In vivo evaluation of an electroenzymatic glucose sensor implanted in subcutaneous tissue. Biosensors & Bioelectronics, 7:709-714.

Kawagoe et al. 1991. Enzyme-modified organic conducting salt microelectrode, Anal. Chem. 63:2961-2965.
Kerner et al. "The function of a hydrogen peroxide-detecting electroenzymatic glucose electrode is markedly impaired in human sub-cutaneous tissue and plasma," Biosensors & Bioelectronics, 8:473-482 (1993).
Maidan et al. 1992. Elimination of Electrooxidizable Interferent-Produced Currents in Amperometric Biosensors, Analytical Chemistry, 64:2889-2896.
Mastrototaro et al. "An electroenzymatic glucose sensor fabricated on a flexible substrate," Sensors and Actuators B, 5:139-44 (1991).
McKean, et al. Jul. 7, 1988. A Telemetry Instrumentation System for Chronically Implanted Glucose and Oxygen Sensors. Transactions on Biomedical Engineering 35:526-532.
Moatti-Sirat et al. 1992. Towards continuous glucose monitoring: in vivo evaluation of a miniaturized glucose sensor implanted for several days in rat subcutaneous tissue. Diabetologia 35:224-230.
Murphy, et al. 1992. Polymer membranes in clinical sensor applications. II. The design and fabrication of permselective hydrogels for electrochemical devices, Biomaterials, 13(14):979-990.
Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.
Pegoraro et al. 1995. Gas transport properties of siloxane polyurethanes, Journal of Applied Polymer Science, 57:421-429.
Pickup et al. "Implantable glucose sensors: choosing the appropriate sensor strategy," Biosensors, 3:335-346 (1987/88).
Pickup et al. "In vivo molecular sensing in diabetes mellitus: an implantable glucose sensor with direct electron transfer," Diabetologia, 32:213-217 (1989).
Pishko et al. "Amperometric glucose microelectrodes prepared through immobilization of glucose oxidase in redox hydrogels," Anal. Chem., 63:2268-72 (1991).
Poitout, et al. 1991. In Vitro and In Vivo Evaluation in Dogs of a Miniaturized Glucose Sensor, ASAIO Transactions, 37:M298-M300.
Reach et al. 1992. Can continuous glucose monitoring be used for the treatment of diabetes? Analytical Chemistry 64(5):381-386.
Rebrin et al. "Automated feedback control of subcutaneous glucose concentration in diabetic dogs," Diabetologia, 32:573-76 (1989).
Sakakida et al. 1993. Ferrocene-Mediated Needle Type Glucose Sensor Covered with Newly Designed Biocompatible Membran, Sensors and Actuators B 13-14:319-322.
Shaw et al. "In vitro testing of a simply constructed, highly stable glucose sensor suitable for implantation in diabetic patients," Biosensors & Bioelectronics, 6:401-406 (1991).
Shichiri et al. 1985. Needle-type Glucose Sensor for Wearable Artificial Endocrine Pancreas in Implantable Sensors 197-210.
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Shichiri et al., 1989. Membrane Design for Extending the Long-Life of an Implantable Glucose Sensor. Diab. Nutr. Metab. 2:309-313.
Shults et al. 1994. A telemetry-instrumentation system for monitoring multiple subcutaneously implanted glucose sensors. IEEE Transactions on Biomedical Engineering 41(10):937-942.
Sokol et al. 1980, Immobilized-enzyme rate-determination method for glucose analysis, Clin. Chem. 26(1):89-92.
Sternberg et al. 1988. Study and Development of Multilayer Needle-type Enzyme-based Glucose Microsensors. Biosensors 4:27-40.
Takegami et al. 1992. Pervaporation of ethanol water mixtures using novel hydrophobic membranes containing polydimethylsiloxane, Journal of Membrance Science, 75(93-105).
Thompson et al., In Vivo Probes: Problems and Perspectives, Department of Chemistry, University of Toronto, Canada, pp. 255-261, 1986.
Turner and Pickup, "Diabetes mellitus: biosensors for research and management," *Biosensors*, 1:85-115 (1985).
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, pp. 117-137.
Velho et al. 1989. Strategies for calibrating a subcutaneous glucose sensor. Biomed Biochim Acta 48(11/12):957-964.
von Woedtke et al. 1989. In situ calibration of implanted electrochemical glucose sensors. Biomed Biochim. Acta 48(11/12):943-952.
Wagner et al. 1998. Continuous amperometric monitoring of glucose in a brittle diabetic chimpanzee with a miniature subcutaneous electrode. Proc. Natl. Acad. Sci. A, 95:6379-6382.
IPRP for PCT/US04/023454 filed Jul. 21, 2004.
IPRP for PCT/US07/03881 filed Feb. 14, 2007.
ISR and WO for PCT/US07/03881 filed Feb. 14, 2007.
Office Action dated Sep. 23, 2005 in U.S. Appl. No. 10/896,639.
Office Action dated Dec. 6, 2005 in U.S. Appl. No. 10/695,636.
Office Action dated Apr. 6, 2006 in U.S. Appl. No. 10/896,639.
Office Action dated May 22, 2006 in U.S. Appl. No. 10/695,636.
Office Action dated Aug. 22, 2006 in U.S. Appl. No. 10/896,639.
Office Action dated Mar. 14, 2007 in U.S. Appl. No. 10/695,636.
Office Action dated Apr. 11, 2007 in U.S. Appl. No. 10/896,639.
Office Action dated Oct. 5, 2007 in U.S. Appl. No. 10/896,639.
Office Action dated Dec. 3, 2008 in U.S. Appl. No. 11/675,063.
Office Action dated Jan. 23, 2009 in U.S. Appl. No. 11/404,417.
Office Action dated Jun. 10, 2009 in U.S. Appl. No. 11/675,063.
Office Action dated Apr. 1, 2007 in U.S. Appl. No. 10/896,639.
International Search Report and Written Opinion received in Appln. No. PCT/US07/03881, mailed Jan. 4, 2008.

* cited by examiner

FIG. 5A - PRIOR ART

OXYGEN ENHANCING MEMBRANE SYSTEMS FOR IMPLANTABLE DEVICES

RELATED APPLICATION

This application is a divisional of U.S. application Ser. No. 10/896,639 filed Jul. 21, 2004, now U.S. Pat. No. 7,379,765 the contents of which are hereby incorporated by reference in their entirety.

FIELD OF THE INVENTION

The present invention relates generally to systems and methods for increasing oxygen availability in implantable devices.

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events.

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) is induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically utilizes uncomfortable finger pricking methods. Due to the lack of comfort and convenience, a diabetic normally only measures his or her glucose level two to four times per day. Unfortunately, these time intervals are spread so far apart that the diabetic likely finds out too late, sometimes incurring dangerous side effects, of a hyperglycemic or hypoglycemic condition. In fact, it is not only unlikely that a diabetic will take a timely SMBG value, but additionally the diabetic will not know if their blood glucose value is going up (higher) or down (lower) based on conventional methods.

Consequently, a variety of transdermal and implantable electrochemical sensors are being developed for continuously detecting and/or quantifying blood glucose values. Many implantable glucose sensors suffer from complications within the body and provide only short-term or less-than-accurate sensing of blood glucose. Similarly, transdermal sensors have problems in accurately sensing and reporting back glucose values continuously over extended periods of time. Some efforts have been made to obtain blood glucose data from implantable devices and retrospectively determine blood glucose trends for analysis; however these efforts do not aid the diabetic in determining real-time blood glucose information. Some efforts have also been made to obtain blood glucose data from transdermal devices for prospective data analysis, however similar problems have been observed.

SUMMARY OF THE PREFERRED EMBODIMENTS

Sensors that can provide accurate, real-time information under ischemic conditions are therefore desirable.

Accordingly, in a first embodiment, an electrochemical sensor for determining a presence or a concentration of an analyte in a fluid is provided, the sensor including a membrane system including an enzyme domain including an enzyme that reacts with the analyte in the fluid as it passes through the enzyme domain; and a working electrode including a conductive material, wherein the working electrode is configured to measure a product of a reaction of the enzyme with the analyte, wherein the membrane system includes a polymer material with a high oxygen solubility.

In an aspect of the first embodiment, the enzyme domain includes a polymer material with a high oxygen solubility.

In an aspect of the first embodiment, the polymer material is selected from the group consisting of silicone, fluorocarbon, and perfluorocarbon.

In an aspect of the first embodiment, the sensor further includes a resistance domain configured to restrict a flow of the analyte therethrough, wherein the resistance domain is located more distal to the working electrode than the enzyme domain, and wherein the resistance domain includes a polymer material with a high oxygen solubility.

In an aspect of the first embodiment, the resistance domain includes a polymer material selected from the group consisting of silicone, fluorocarbon, and perfluorocarbon.

In an aspect of the first embodiment, the sensor further includes a cell impermeable domain that is substantially impermeable to cells, wherein the cell impermeable domain is located more distal to the working electrode than the enzyme domain, and wherein the cell impermeable domain includes a polymer material with a high oxygen solubility.

In an aspect of the first embodiment, the cell impermeable domain includes a polymer material selected from the group consisting of silicone, fluorocarbon, and perfluorocarbon.

In an aspect of the first embodiment, the sensor further includes a cell disruptive domain that includes a substantially porous structure, wherein the cell disruptive domain is located more distal to the working electrode than the enzyme domain, and wherein the cell disruptive domain includes a polymer material with high oxygen solubility.

In an aspect of the first embodiment, the cell impermeable domain includes a polymer material selected from the group consisting of silicone, fluorocarbon, and perfluorocarbon.

In an aspect of the first embodiment, the sensor further includes an interference domain configured to limit or block interfering species, wherein the interference domain is located more proximal to the working electrode than the enzyme domain, and wherein the interference domain includes a polymer material with a high oxygen solubility.

In an aspect of the first embodiment, the interference domain includes a polymer material selected from the group consisting of silicone, fluorocarbon, and perfluorocarbon.

In an aspect of the first embodiment, the sensor further includes an electrolyte domain configured to provide hydrophilicity at the working electrode, wherein the electrolyte domain is located more proximal to the working electrode than the enzyme domain, and wherein the electrolyte domain includes a polymer material with a high oxygen solubility.

In an aspect of the first embodiment, the electrolyte domain includes a polymer material selected from the group consisting of silicone, fluorocarbon, and perfluorocarbon.

In a second embodiment, an analyte sensing device configured for implantation into a tissue of a host is provided, the device including an oxygen-utilizing source; a membrane system configured to provide at least one function selected from the group consisting of protection of the device from a biological environment; diffusion resistance of an analyte; a catalyst for enabling an enzymatic reaction; and limitation of interfering species; wherein the membrane system includes a polymer material with a high oxygen solubility, wherein the membrane system is adjacent to the oxygen-utilizing source.

In an aspect of the second embodiment, the oxygen-utilizing source includes an enzyme.

In an aspect of the second embodiment, the membrane system includes the polymer material with the high oxygen solubility, wherein the polymer material is substantially continuously situated between the enzyme and the tissue.

In an aspect of the second embodiment, the oxygen-utilizing source includes an electroactive surface.

In an aspect of the second embodiment, the membrane system includes the polymer material with the high oxygen solubility, wherein the polymer material is substantially continuously situated between the electroactive surface and the tissue.

In an aspect of the second embodiment, the oxygen-utilizing source includes cells.

In an aspect of the second embodiment, the membrane system includes the polymer material with the high oxygen solubility, wherein the polymer material is substantially continuously situated between the cells and the tissue.

In an aspect of the second embodiment, the polymer material is selected from the group consisting of silicone, fluorocarbon, and perfluorocarbon.

BRIEF DESCRIPTION OF THE DRAWINGS

FIG. 5A is a schematic diagram of oxygen concentration profiles through a prior art membrane.

DETAILED DESCRIPTION OF THE PREFERRED EMBODIMENT

Figure 1:
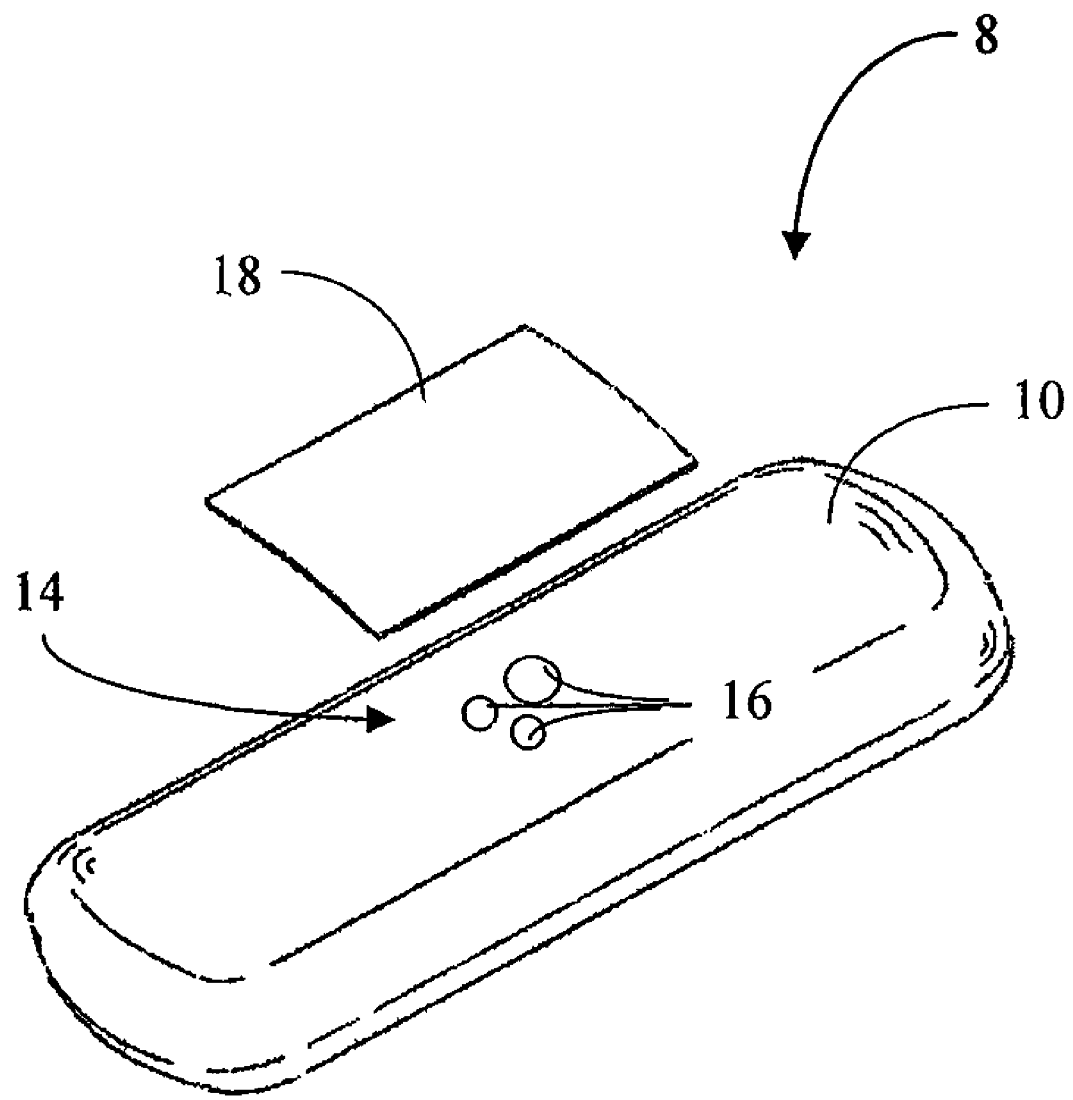
FIG. 1 is an exploded perspective view of an implantable glucose sensor in one exemplary embodiment.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

DEFINITIONS

In order to facilitate an understanding of the preferred embodiments, a number of terms are defined below.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; camitine; camosinase; CD4; ceruloplasmin; chenodeoxycholic acid; chloroquine; cholesterol; cholinesterase; conjugated 1-βhydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; ethanol;

cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "operable connection," "operably connected," and "operably linked" as used herein are broad terms and are used in their ordinary sense, including, without limitation, one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably linked" to the electronic circuitry.

The term "host" as used herein is a broad term and is used in its ordinary sense, including, without limitation, mammals, particularly humans.

The terms "electrochemically reactive surface" and "electroactive surface" as used herein are broad terms and are used in their ordinary sense, including, without limitation, the surface of an electrode where an electrochemical reaction takes place. As one example, a working electrode measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. The sensing region generally comprises a non-conductive body, a working electrode, a reference electrode, and/or a counter electrode (optional) passing through and secured within the body forming electrochemically reactive surfaces on the body, an electronic connective means at another location on the body, and a multi-domain membrane affixed to the body and covering the electrochemically reactive surface.

The terms "raw data stream" and "data stream," as used herein, are broad terms and are used in their ordinary sense, including, without limitation, an analog or digital signal directly related to the measured glucose concentration from the glucose sensor. In one example, the raw data stream is digital data in "counts" converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term "counts," as used herein, is a broad term and is used in its ordinary sense, including, without limitation, a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The term "electrical potential," as used herein, is a broad term and is used in its ordinary sense, including, without limitation, the electrical potential difference between two points in a circuit which is the cause of the flow of a current.

The term "ischemia," as used herein, is a broad term and is used in its ordinary sense, including, without limitation, local and temporary deficiency of blood supply due to obstruction of circulation to a part (for example, sensor). Ischemia can be caused by mechanical obstruction (for example, arterial narrowing or disruption) of the blood supply, for example.

The term "system noise," as used herein, is a broad term and is used in its ordinary sense, including, without limitation, unwanted electronic or diffusion-related noise which can include Gaussian, motion-related, flicker, kinetic, or other white noise, for example.

The terms "signal artifacts" and "transient non-glucose related signal artifacts," as used herein, are broad terms and are used in their ordinary sense, including, without limitation, signal noise that is caused by substantially non-glucose reaction rate-limiting phenomena, such as ischemia, pH changes, temperature changes, pressure, and stress, for example. Signal artifacts, as described herein, are typically transient and are characterized by higher amplitude than system noise.

The terms "low noise," as used herein, is a broad term and is used in its ordinary sense, including, without limitation, noise that substantially decreases signal amplitude.

The terms "high noise" and "high spikes," as used herein, are broad terms and are used in their ordinary sense, including, without limitation, noise that substantially increases signal amplitude.

The term "silicone composition" as used herein is a broad term and is used in its ordinary sense, including, without limitation, a composition of matter that comprises polymers having at least silicon and oxygen atoms in the backbone.

The phrase "distal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell disruptive domain is positioned farther from the sensor, then that domain is distal to the sensor.

The phrase "proximal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell impermeable domain is positioned nearer to the sensor, then that domain is proximal to the sensor.

The terms "interferants" and "interfering species," as used herein, are broad terms and are used in their ordinary sense, including, but not limited to, effects and/or species that interfere with the measurement of an analyte of interest in a sensor to produce a signal that does not accurately represent the analyte measurement. In an electrochemical sensor, interfering species can include compounds with an oxidation potential that overlaps with that of the analyte to be measured.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees, Centigrade).

Overview

Membrane systems of the preferred embodiments are suitable for use with implantable devices in contact with a biological fluid. For example, the membrane systems can be utilized with implantable devices such as devices for monitoring and determining analyte levels in a biological fluid, for example, glucose levels for individuals having diabetes. In some embodiments, the analyte-measuring device is a continuous device. Alternatively, the device can analyze a plurality of intermittent biological samples. The analyte-measuring device can use any method of analyte-measurement, including enzymatic, chemical, physical, electrochemical, spectrophotometric, polarimetric, calorimetric, radiometric, or the like.

Although some of the description that follows is directed at glucose-measuring devices, including the described membrane systems and methods for their use, these membrane systems are not limited to use in devices that measure or monitor glucose. These membrane systems are suitable for use in a variety of devices, including, for example, those that detect and quantify other analytes present in biological fluids (including, but not limited to, cholesterol, amino acids, alcohol, galactose, and lactate), cell transplantation devices (see, for example, U.S. Pat. Nos. 6,015,572, 5,964,745, and 6,083,523), drug delivery devices (see, for example, U.S. Pat. Nos. 5,458,631, 5,820,589, and 5,972,369), and the like. Preferably, implantable devices that include the membrane systems of the preferred embodiments are implanted in soft tissue, for example, abdominal, subcutaneous, and peritoneal tissues, the brain, the intramedullary space, and other suitable organs or body tissues.

In addition to the glucose-measuring device described below, the membrane systems of the preferred embodiments can be employed with a variety of known glucose measuring-devices. In some embodiments, the electrode system can be used with any of a variety of known in vivo analyte sensors or monitors, such as U.S. Pat. No. 6,001,067 to Shults et al.; U.S. Pat. No. 6,702,857 to Brauker et al.; U.S. Pat. No. 6,212,416 to Ward el al.; U.S. Pat. No. 6,119,028 to Schulman et al.; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al.; U.S. Pat. No. to 5,985,129 to Gough et al.; WO Patent Application Publication No. 04/021877 to Caduff; U.S. Pat. No. 5,494,562 to Maley et al.; U.S. Pat. No. 6,120,676 to Heller et al.; and U.S. Pat. No. 6,542,765 to Guy et al., each of which are incorporated in there entirety herein by reference. In general, it is understood that the disclosed embodiments are applicable to a variety of continuous glucose measuring device configurations.

FIG. 1 is an exploded perspective view of one exemplary embodiment comprising an implantable glucose sensor 10 that utilizes amperometric electrochemical sensor technology to measure glucose. In this exemplary embodiment, a body 12 with a sensing region 14 includes an electrode system 16 and sensor electronics, which are described in more detail with reference to FIG. 2.

In this embodiment, the electrode system 16 is operably connected to the sensor electronics (FIG. 2) and includes electroactive surfaces, which are covered by a membrane system 18. The membrane system 18 is disposed over the electroactive surfaces of the electrode system 16 and provides one or more of the following functions: 1) protection of the exposed electrode surface from the biological environment (cell impermeable domain); 2) diffusion resistance (limitation) of the analyte (resistance domain); 3) a catalyst for enabling an enzymatic reaction (enzyme domain); 4) limitation or blocking of interfering species (interference domain); and/or 5) hydrophilicity at the electrochemically reactive surfaces of the sensor interface (electrolyte domain), for example, as described in co-pending U.S. patent application Ser. No. 10/838,912, filed May 3, 2004 and entitled "IMPLANTABLE ANALYTE SENSOR," the contents of which are hereby incorporated herein by reference in their entirety. The membrane system can be attached to the sensor body 12 by mechanical or chemical methods such as are described in co-pending U.S. Patent Application MEMBRANE ATTACHMENT and U.S. patent application Ser. No. 10/838,912 filed May 3, 2004 and entitled, "IMPLANTABLE ANALYTE SENSOR", the contents of which are hereby incorporated herein by reference in their entirety.

Figure 3:
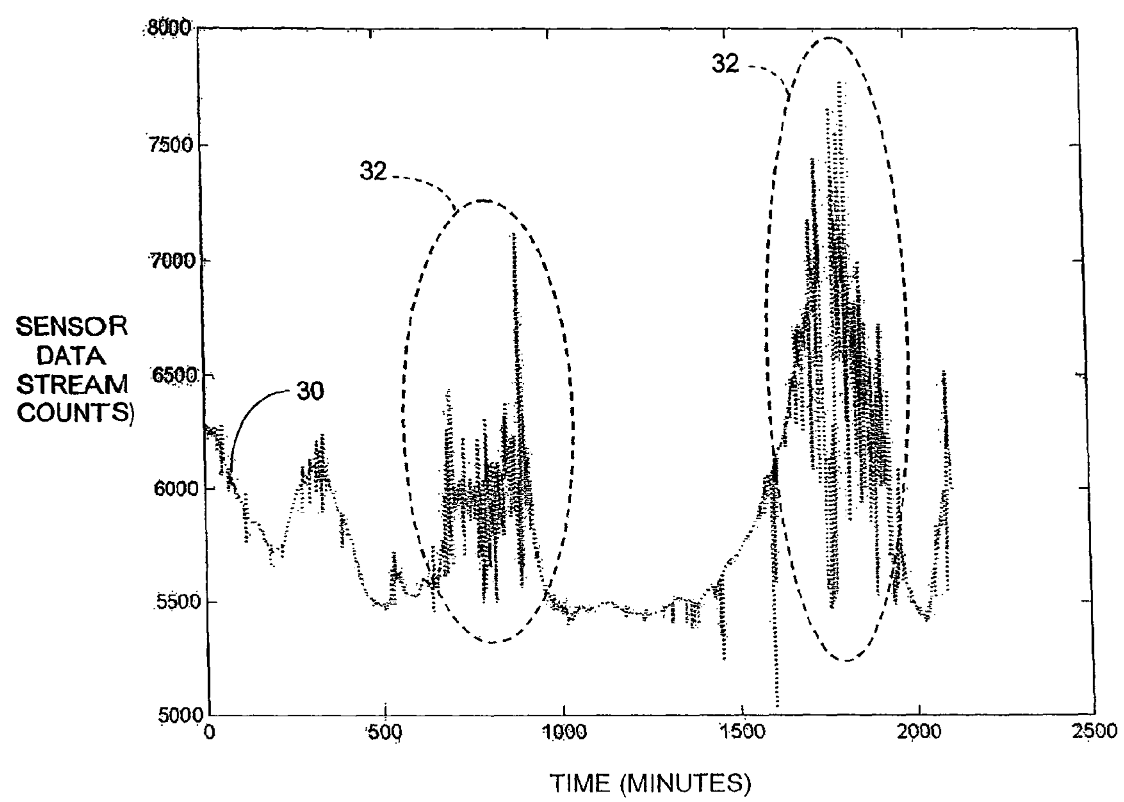
FIG. 3 is a graph that shows a raw data stream obtained from a glucose sensor over a 36-hour time span in one example.
Figure 4:
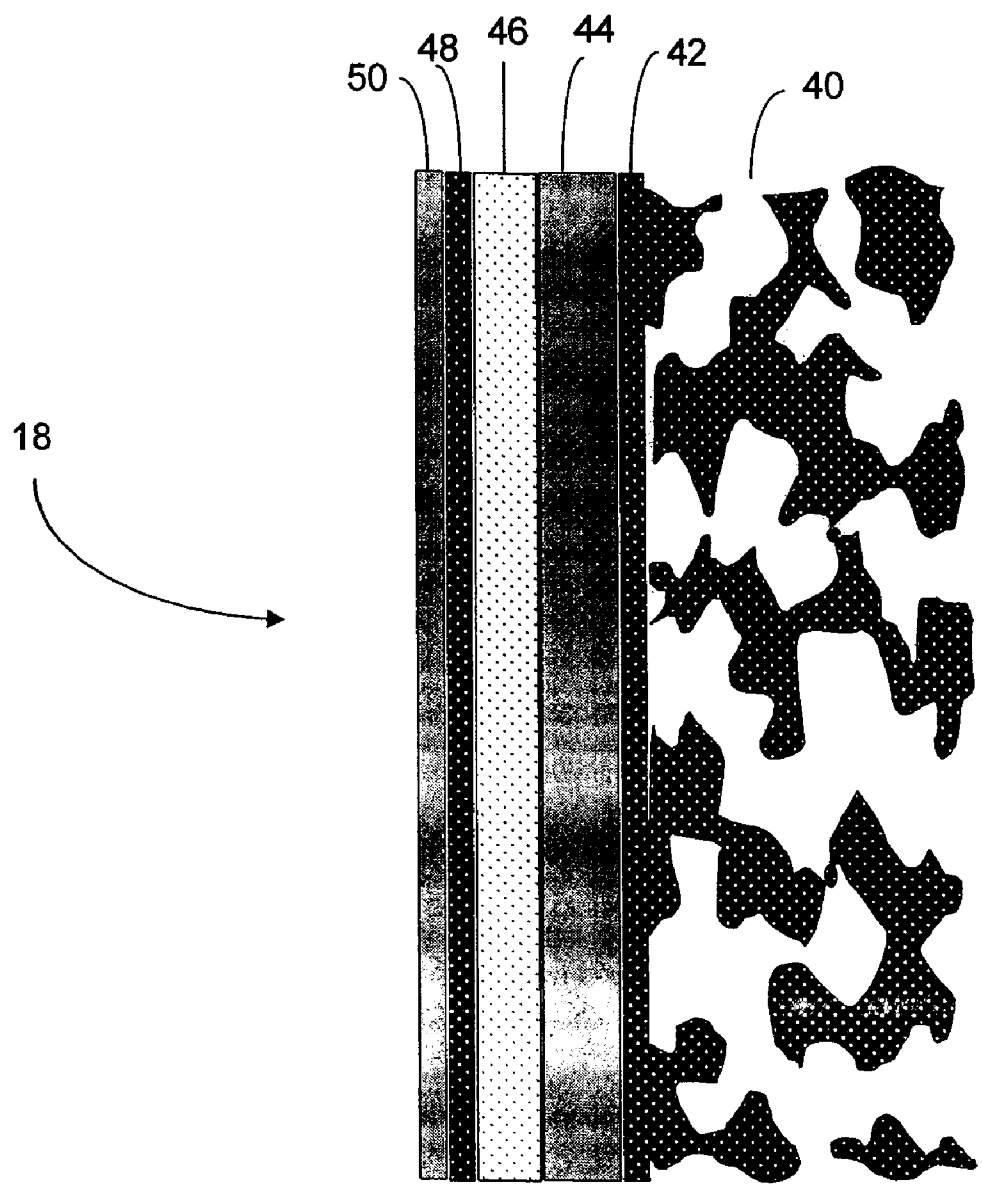
FIG. 4 is a schematic illustration of a membrane system of the device of FIG. 1.
Figure 5B:
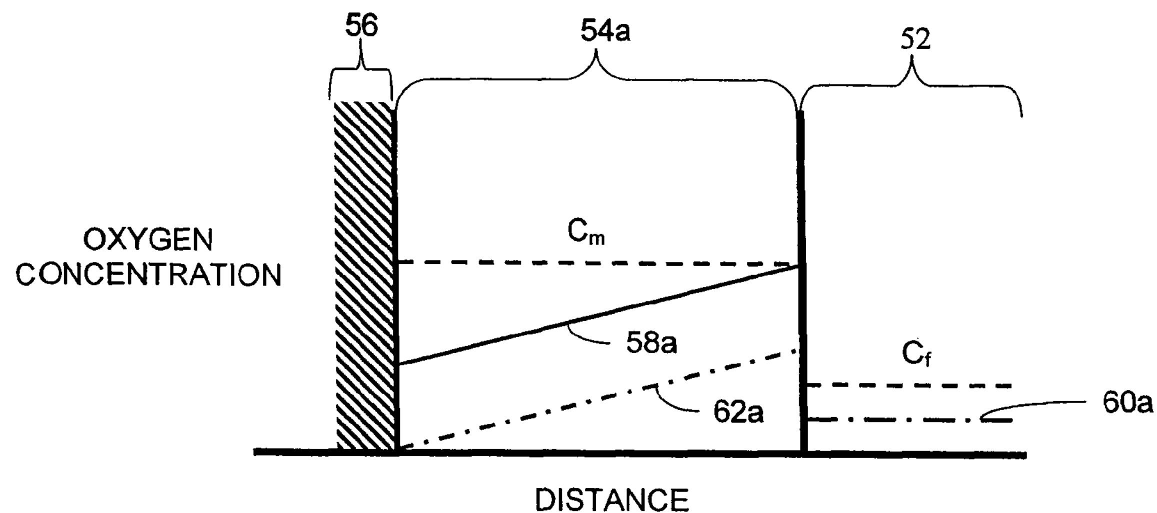
FIG. 5B is a schematic diagram of oxygen concentration profiles through the membrane system of the preferred embodiments.
Figure 5B:
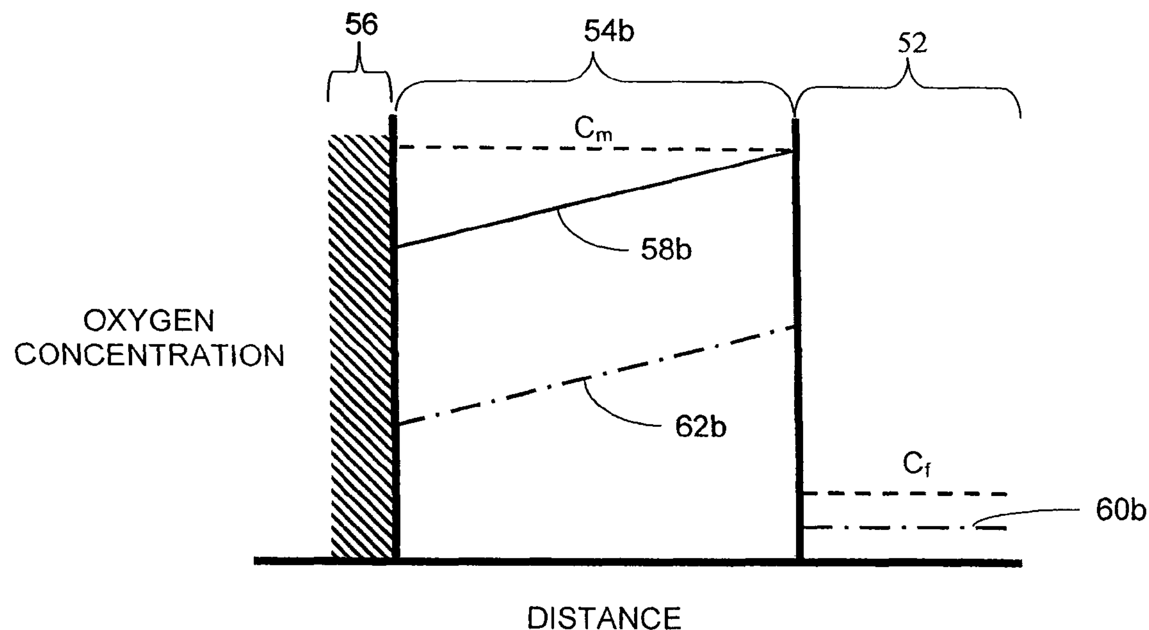

The membrane system 18 of the preferred embodiments, which are described in more detail below with reference to FIGS. 4 and 5, is formed at least partially from materials with high oxygen solubility. These materials act as a high oxygen soluble domain, dynamically retaining a high availability of oxygen that can be used to compensate for the local oxygen deficit during times of transient ischemia, which is described in more detail below and with reference to FIG. 3. As a result, the membrane systems of the preferred embodiments enable glucose sensors and other implantable devices such as cell transplantation devices to function in the subcutaneous space even during local transient ischemia.

In some embodiments, the electrode system 16, which is located on or within the sensing region 14, is comprised of at least a working and a reference electrode with an insulating material disposed therebetween. In some alternative embodiments, additional electrodes can be included within the electrode system, for example, a three-electrode system (working, reference, and counter electrodes) and/or including an additional working electrode (which can be used to generate oxygen, measure an additional analyte, or can be configured as a baseline subtracting electrode, for example).

In the exemplary embodiment of FIG. 1, the electrode system includes three electrodes (working, counter, and reference electrodes), wherein the counter electrode is provided to balance the current generated by the species being measured at the working electrode. In the case of a glucose oxidase based glucose sensor, the species being measured at the working electrode is $H_2O_2$. Glucose oxidase, GOX, catalyzes the conversion of oxygen and glucose to hydrogen peroxide and gluconate according to the following reaction:

$$GOX+Glucose+O_2 \rightarrow Gluconate+H_2O_2+reduced\ GOX$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule O2). In such embodiments, because the counter electrode utilizes oxygen as an electron acceptor, the most likely reducible species for this system are oxygen or enzyme generated peroxide. There are two main pathways by which oxygen can be consumed at the counter electrode. These pathways include a four-electron pathway to produce hydroxide and a two-electron pathway to produce hydrogen peroxide. In addition to the counter electrode, oxygen is further consumed by the reduced glucose oxidase within the enzyme domain. Therefore, due to the oxygen consumption by both the enzyme and the counter electrode, there is a net consumption of oxygen within the electrode system. Theoretically, in the domain of the working electrode there is significantly less net loss of oxygen than in the region of the counter electrode. In addition, there is a close correlation between the ability of the counter electrode to maintain current balance and sensor function.

In general, in electrochemical sensors wherein an enzymatic reaction depends on oxygen as a co-reactant, depressed function or inaccuracy can be experienced in low oxygen environments, for example in vivo. Subcutaneously implanted devices are especially susceptible to transient ischemia that can compromise device function; for example, because of the enzymatic reaction required for an implantable amperometric glucose sensor, oxygen must be in excess over glucose in order for the sensor to effectively function as a glucose sensor. If glucose becomes in excess, the sensor turns into an oxygen sensitive device. In vivo, glucose concentration can vary from about one hundred times or more that of the oxygen concentration. Consequently, oxygen becomes a limiting reactant in the electrochemical reaction and when insufficient oxygen is provided to the sensor, the sensor is unable to accurately measure glucose concentration. Those skilled in the art interpret oxygen limitations resulting in depressed function or inaccuracy as a problem of availability of oxygen to the enzyme and/or counter electrode. Oxygen limitations can also be seen during periods of transient ischemia that occur, for example, under certain postures or when the region around the implanted sensor is compressed so that blood is forced out of the capillaries. Such ischemic periods observed in implanted sensors can last for many minutes or even an hour or longer.

Figure 2:
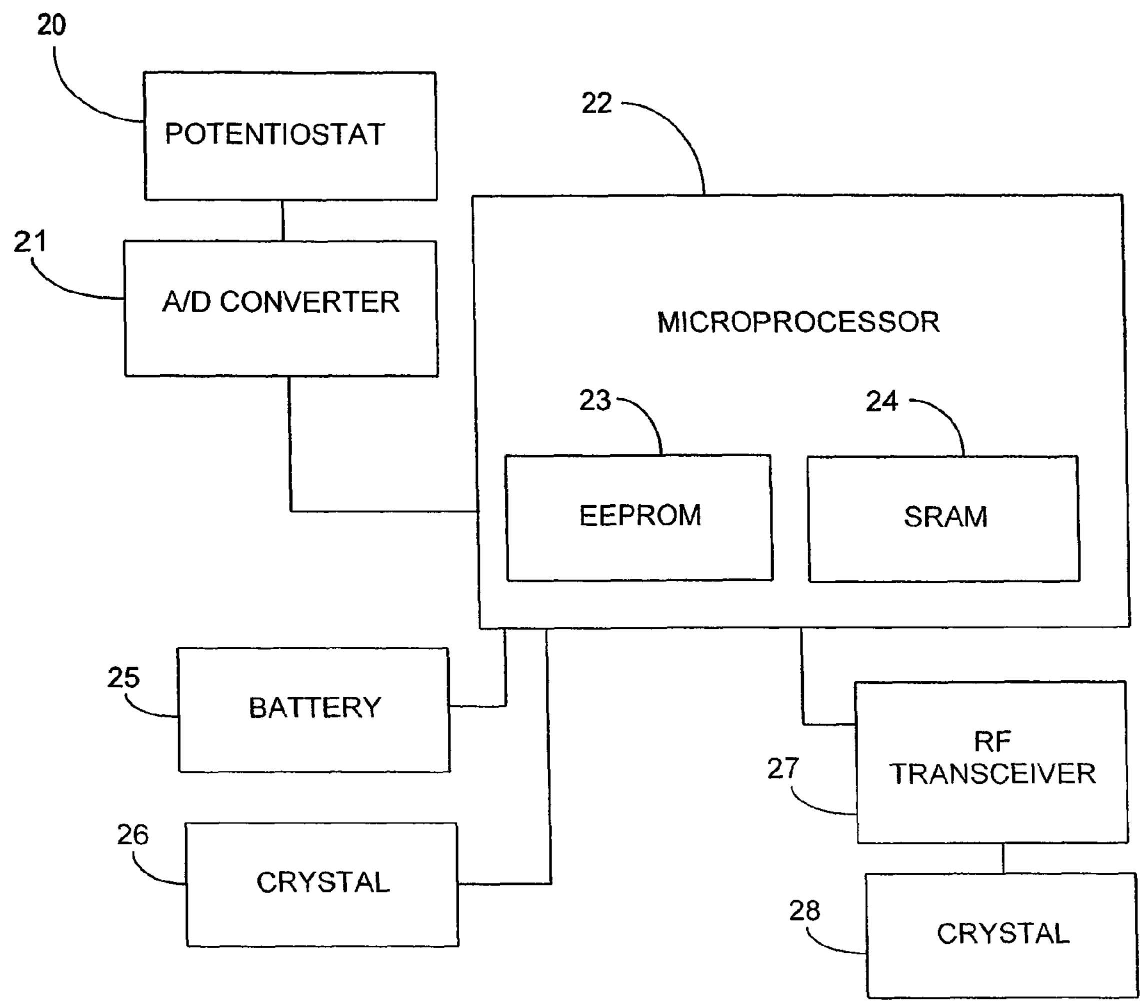
FIG. 2 is a block diagram that illustrates the sensor electronics in one embodiment; however a variety of sensor electronics configurations can be implemented with the preferred embodiments.

FIG. 2 is a block diagram that illustrates sensor electronics in one exemplary embodiment; one skilled in the art appreciates, however, a variety of sensor electronics configurations can be implemented with the preferred embodiments. In this embodiment, a potentiostat 20 is shown, which is operatively connected to electrode system 16 (FIG. 1) to obtain a current value, and includes a resistor (not shown) that translates the current into voltage. The A/D converter 21 digitizes the analog signal into "counts" for processing. Accordingly, the resulting raw data signal in counts is directly related to the current measured by the potentiostat.

A microprocessor 22 is the central control unit that houses EEPROM 23 and SRAM 24, and controls the processing of the sensor electronics. The alternative embodiments can utilize a computer system other than a microprocessor to process data as described herein. In some alternative embodiments, an application-specific integrated circuit (ASIC) can be used for some or all the sensor's central processing. EEPROM 23 provides semi-permanent storage of data, storing data such as sensor ID and programming to process data signals (for example, programming for data smoothing such as described elsewhere herein). SRAM 24 is used for the system's cache memory, for example for temporarily storing recent sensor data.

The battery 25 is operatively connected to the microprocessor 22 and provides the power for the sensor. In one embodiment, the battery is a Lithium Manganese Dioxide battery, however any appropriately sized and powered battery can be used. In some embodiments, a plurality of batteries can be used to power the system. Quartz Crystal 26 is operatively connected to the microprocessor 22 and maintains system time for the computer system.

The RF Transceiver 27 is operably connected to the microprocessor 22 and transmits the sensor data from the sensor to a receiver. Although a RF transceiver is shown here, some other embodiments can include a wired rather than wireless connection to the receiver. In yet other embodiments, the sensor can be transcutaneously connected via an inductive coupling, for example. The quartz crystal 28 provides the system time for synchronizing the data transmissions from the RF transceiver. The transceiver 27 can be substituted with a transmitter in one embodiment.

Although FIGS. 1 to 2 and associated text illustrate and describe one exemplary embodiment of an implantable glucose sensor, the electrode system, electronics and its method of manufacture of the preferred embodiments described below can be implemented on any known electrochemical sensor, including those described in co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; "OPTIMIZED SENSOR GEOMETRY FOR AN IMPLANTABLE GLUCOSE SENSOR"; U.S. application Ser. No. 10/633,367 filed Aug. 1, 2003 entitled, "SYSTEM AND METHODS FOR PROCESSING ANALYTE SENSOR DATA", the contents of each of which are hereby incorporated by reference in their entireties.

FIG. 3 is a graph that shows a raw data stream obtained from a glucose sensor with a conventional membrane system. The x-axis represents time in minutes. The y-axis represents sensor data in counts. In this example, sensor output in counts is transmitted every 30 seconds. The raw data stream 30 includes substantially smooth sensor output in some portions, however other portions exhibit transient non-glucose related signal artifacts 32.

The raw data stream 30 includes substantially smooth sensor output in some portions, however other portions exhibit erroneous or transient non-glucose related signal artifacts 32. Particularly, referring to the signal artifacts 32, it is believed that effects of local ischemia on prior art electrochemical sensors creates erroneous (non-glucose) signal values due to oxygen deficiencies either at the enzyme within the membrane system and/or at the counter electrode on the electrode surface.

In one situation, when oxygen is deficient relative to the amount of glucose, the enzymatic reaction is limited by oxygen rather than glucose. Thus, the output signal is indicative of the oxygen concentration rather than the glucose concentration, producing erroneous signals. Additionally, when an enzymatic reaction is rate-limited by oxygen, glucose is expected to build up in the membrane because it is not completely catabolized during the oxygen deficit. When oxygen is again in excess, there is also excess glucose due to the transient oxygen deficit. The enzyme rate then speeds up for a short period until the excess glucose is catabolized, resulting in spikes of non-glucose related increased sensor output. Accordingly, because excess oxygen (relative to glucose) is necessary for proper sensor function, transient ischemia can result in a loss of signal gain in the sensor data.

In another situation, oxygen deficiency can be seen at the counter electrode when insufficient oxygen is available for reduction, which thus affects the counter electrode in that it is unable to balance the current coming from the working electrode. When insufficient oxygen is available for the counter electrode, the counter electrode can be driven in its electrochemical search for electrons all the way to its most negative value, which can be ground, or 0.0 V, which causes the reference to shift, reducing the bias voltage such as is described in more detail below. In other words, a common result of ischemia is seen as a drop off in sensor current as a function of glucose concentration (for example, lower sensitivity). This occurs because the working electrode no longer oxidizes all of the $H_2O_2$ arriving at its surface because of the reduced bias. In some extreme circumstances, an increase in glucose can produce no increase in current or even a decrease in current.

In some situations, transient ischemia can occur at high glucose levels, wherein oxygen can become limiting to the enzymatic reaction, resulting in a non-glucose dependent downward trend in the data. In some situations, certain movements or postures taken by the patient can cause transient signal artifacts as blood is squeezed out of the capillaries, resulting in local ischemia, and causing non-glucose dependent signal artifacts. In some situations, oxygen can also become transiently limited due to contracture of tissues around the sensor interface. This is similar to the blanching of skin that can be observed when one puts pressure on it. Under such pressure, transient ischemia can occur in both the epidermis and subcutaneous tissue. Transient ischemia is common and well tolerated by subcutaneous tissue. However, such ischemic periods can cause an oxygen deficit in implanted devices that can last for many minutes or even an hour or longer.

Although some examples of the effects of transient ischemia on a prior art glucose sensor are described above, similar effects can be seen with analyte sensors that use alternative catalysts to detect other analytes, for example, amino acids (amino acid oxidase), alcohol (alcohol oxidase), galactose (galactose oxidase), lactate (lactate oxidase), and cholesterol (cholesterol oxidase), or the like.

Membrane Systems of the Preferred Embodiments

In order to overcome the effects of transient ischemia, the membrane systems 18 of the preferred embodiments include materials with high oxygen solubility. These materials increase the local amount of oxygen to aid in compensating for local oxygen deficits during ischemic conditions. As a result, the membrane systems of the preferred embodiments enable analyte sensors and other devices such as cell transplantation devices to function in the subcutaneous space even during local transient ischemia.

The phrases "high oxygen solubility" and "high oxygen soluble" as used herein are broad phrases and are used in their ordinary sense, including, without limitation, a domain or material property that includes higher oxygen solubility than aqueous media so that it concentrates oxygen from the biological fluid surrounding the membrane system. In some preferred embodiments, a high oxygen solubility polymer has at least about 3× higher oxygen solubility than aqueous media, more preferably at least about 4×, 5×, or 6× higher oxygen solubility than aqueous media, and most preferably at least about 7×, 8×, 9×, 10× or more higher oxygen solubility than aqueous media. In one embodiment, high oxygen solubility is defined as having higher oxygen solubility than at least one of a hydrocarbonaceous polymer and an oxyhydrocarbon polymer (a hydrocarbonaceous polymer is a polymeric material consisting of carbon and hydrogen atoms and an oxyhydrocarbonaceous polymer is a polymeric material consisting of carbon, hydrogen, and oxygen atoms). Oxygen solubility can be measured using any known technique, for example by removing the oxygen from the polymer (namely, solution) via at least three Freeze-Pump-Thaw cycles and then measuring the resultant oxygen (for example, using a manometer).

Oxygen permeability (Dk) is calculated as diffusion multiplied by solubility. Oxygen Permeability is conveniently reported in units of Barrers (1 Barrer=$10^{-10}$ $cm^3$ $O_2$ (STP) $cm/cm^2s$ cmHg). Insulating materials of preferred embodiments that have a high oxygen permeability typically have an oxygen permeability of from about 1 Barrer or less to about 1000 Barrers or more, preferably from about 1, 2, 3, 4, 5, 6, 7, 8, 9, 10, 15, 20, 25, 30, 35, 40, 45, 50, 55, 60, 65, 70, 75, 80, 85, 90, 95, or 100 Barrers to about 125, 150, 175, 200, 225, 250, 275, 300, 325, 350, 375, 400, 425, 450, 475, 500, 550, 600, 650, 700, 750, 800, 850, 900, or 950 Barrers.

In one exemplary embodiment, the properties of silicone (and/or silicone compositions) inherently enable materials formed from silicone to act as a high oxygen solubility domain. Utilization of a high oxygen soluble material in an electrochemical sensor is advantageous because it is believed to dynamically retain high oxygen availability to oxygen-utilizing sources (for example, an enzyme and/or a counter electrode of an electrochemical cell).

As described below with reference to FIG. 4, the membrane system 18 can include two or more domains that cover an implantable device, for example, an implantable glucose sensor. In the example of an implantable enzyme-based electrochemical glucose sensor, the membrane prevents direct contact of the biological fluid sample with the electrodes, while controlling the permeability of selected substances (for example, oxygen and glucose) present in the biological fluid through the membrane for reaction in an enzyme rich domain with subsequent electrochemical reaction of formed products at the electrodes.

The membrane systems of preferred embodiments are constructed of two or more domains. The multi-domain membrane can be formed from one or more distinct layers and can comprise the same or different materials. The term "domain" is a broad term and is used in its ordinary sense, including, without limitation, a single homogeneous layer or region that incorporates the combined functions one or more domains, or a plurality of layers or regions that each provide one or more of the functions of each of the various domains.

FIG. 4 is an illustration of a membrane system in one preferred embodiment. The membrane system 18 can be used with a glucose sensor such, as is described above with reference to FIG. 1. In this embodiment, the membrane system 18 includes a cell disruptive domain 40 most distal of all domains from the electrochemically reactive surfaces, a cell impermeable domain 42 less distal from the electrochemically reactive surfaces than the cell disruptive domain, a resistance domain 44 less distal from the electrochemically reactive surfaces than the cell impermeable domain, an enzyme domain 46 less distal from the electrochemically reactive surfaces than the resistance domain, an interference domain 48 less distal from the electrochemically reactive surfaces than the enzyme domain, and an electrolyte domain 50 adjacent to the electrochemically reactive surfaces. However, it is understood that the membrane system can be modified for use in other devices, by including only two or more of the domains, or additional domains not recited above.

In some embodiments, the membrane system is formed as a homogeneous membrane, namely, a membrane having substantially uniform characteristics from one side of the membrane to the other. However, a membrane can have heterogeneous structural domains, for example, domains resulting from the use of block copolymers (for example, polymers in which different blocks of identical monomer units alternate with each other), but can be defined as homogeneous overall in that each of the above-described domains functions by the preferential diffusion of some substance through the homogeneous membrane.

In the preferred embodiments, one or more of the above-described domains are formed from high oxygen solubility material. Utilization of high oxygen solubility material is advantageous because it is believed to dynamically retain a higher amount of oxygen, which maintains higher oxygen availability to selected locations (for example, the enzyme and/or counter electrode). In some embodiments, the high oxygen soluble material includes silicones, fluorocarbons, perfluorocarbons, or the like. In one embodiment, one or more domains is/are formed from a silicone composition that allows the transport of glucose other such water-soluble molecules (for example, drugs), such as are described in more detail with reference to co-pending U.S. application Ser. No. 10/685,636 filed Oct. 28, 2003 and entitled, "SILICONE COMPOSITION FOR MEMBRANE SYSTEM," the contents of which are hereby incorporated by reference in their entireties.

Cell Disruptive Domain

The cell disruptive domain 40 is positioned most distal to the implantable device and is designed to support tissue ingrowth, to disrupt contractile forces typically found in a foreign body capsule, to encourage vascularity within the membrane, and/or to disrupt the formation of a barrier cell layer. In one embodiment, the cell disruptive domain 40 has an open-celled configuration with interconnected cavities and solid portions, wherein the distribution of the solid portion and cavities of the cell disruptive domain includes a substantially co-continuous solid domain and includes more than one cavity in three dimensions substantially throughout the entirety of the first domain. Cells can enter into the cavities; however they cannot travel through or wholly exist within the solid portions. The cavities allow most substances to pass through, including, for example, cells, and molecules. U.S. Pat. No. 6,702,857, filed Jul. 27, 2001, and entitled "MEMBRANE FOR USE WITH IMPLANTABLE DEVICES" and U.S. patent application Ser. No. 10/647,065, filed Aug. 22, 2003, and entitled, "POROUS MEMBRANES FOR USE WITH IMPLANTABLE DEVICES" describe membranes having a cell disruptive domain.

The cell disruptive domain 40 is preferably formed from high oxygen soluble materials such as polymers formed from silicone, fluorocarbons, perfluorocarbons, or the like. In one embodiment, the cell disruptive domain is formed from a silicone composition with a non-silicon containing hydrophile such as such as polyethylene glycol, propylene glycol, pyrrolidone, esters, amides, carbonates, or polypropylene glycol covalently incorporated or grafted therein. In some alternative embodiments, the cell disruptive domain is formed from polyethylene-co-tetrafluoroethylene, polyolefin, polyester, polycarbonate, biostable polytetrafluoroethylene, homopolymers, copolymers, terpolymers of polytetrafluoroethylene, polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones or block copolymers thereof including, for example, di-block, tri-block, alternating, random and graft copolymers.

In preferred embodiments, the thickness of the cell disruptive domain is from about 10 or less, 20, 30, 40, 50, 60, 70, 80, or 90 microns to about 1500, 2000, 2500, or 3000 or more microns. In more preferred embodiments, the thickness of the cell disruptive domain is from about 100, 150, 200 or 250 microns to about 1000, 1100, 1200, 1300, or 1400 microns. In even more preferred embodiments, the thickness of the cell disruptive domain is from about 300, 350, 400, 450, 500, or 550 microns to about 500, 550, 600, 650, 700, 750, 800, 850, or 900 microns.

The cell disruptive domain is optional and can be omitted when using an implantable device that does not prefer tissue ingrowth, for example, a short-lived device (for example, less than one day to about a week) or one that delivers tissue response modifiers.

Cell Impermeable Domain

The cell impermeable domain 42 is positioned less distal to the implantable device than the cell disruptive domain, and can be resistant to cellular attachment, impermeable to cells, and/or is composed of a biostable material. When the cell impermeable domain is resistant to cellular attachment (for example, attachment by inflammatory cells, such as macrophages, which are therefore kept a sufficient distance from other domains, for example, the enzyme domain), hypochlorite and other oxidizing species are short-lived chemical species in vivo, and biodegradation does not occur. Additionally, the materials preferred for forming this domain are resistant to the effects of these oxidative species and have thus been termed biodurable. See, for example, U.S. Pat. No. 6,702,857, filed Jul. 27, 2001, and entitled "MEMBRANE FOR USE WITH IMPLANTABLE DEVICES" and U.S. patent application Ser. No. 10/647,065, filed Aug. 22, 2003, and entitled, "POROUS MEMBRANES FOR USE WITH IMPLANTABLE DEVICES."

The cell impermeable domain 42 is preferably formed from high oxygen soluble materials such as polymers formed from silicone, fluorocarbons, perfluorocarbons, or the like. In one embodiment, the cell impermeable domain is formed from a silicone composition with a hydrophile such as such as polyethylene glycol, propylene glycol, pyrrolidone, esters, amides, carbonates, or polypropylene glycol covalently incorporated or grafted therein. In some alternative embodiments, the cell impermeable domain is formed from copolymers or blends of copolymers with hydrophilic polymers such as polyvinylpyrrolidone (PVP), polyhydroxyethyl methacrylate, polyvinylalcohol, polyacrylic acid, polyethers such as polyethylene glycol, and block copolymers thereof, including, for example, di-block, tri-block, alternating, random and graft copolymers (block copolymers are discussed in U.S. Pat. Nos. 4,803,243 and 4,686,044).

In preferred embodiments, the thickness of the cell impermeable domain is from about 10 or 15 microns or less to about 125, 150, 175, or 200 microns or more. In more preferred embodiments, the thickness of the cell impermeable domain is from about 20, 25, 30, or 35 microns to about 65, 70, 75, 80, 85, 90, 95, or 100 microns. In even more preferred embodiments, the cell impermeable domain is from about 40 or 45 microns to about 50, 55, or 60 microns thick.

The cell disruptive domain 40 and cell impermeable domain 42 of the membrane system can be formed together as one unitary structure. Alternatively, the cell disruptive and cell impermeable domains 40, 42 of the membrane system can be formed as two layers mechanically or chemically bonded together.

Resistance Domain

The resistance domain 44 is situated more proximal to the implantable device relative to the cell disruptive domain. The resistance domain controls the flux of oxygen and other analytes (for example, glucose) to the underlying enzyme domain. As described in more detail elsewhere herein, there exists a molar excess of glucose relative to the amount of oxygen in blood; that is, for every free oxygen molecule in extracellular fluid, there are typically more than 100 glucose molecules present (see Updike et al., Diabetes Care 5:207-21 (1982)). However, an immobilized enzyme-based sensor employing oxygen as cofactor is supplied with oxygen in non-rate-limiting excess in order to respond linearly to changes in glucose concentration, while not responding to changes in oxygen tension. More specifically, when a glucose-monitoring reaction is oxygen-limited, linearity is not achieved above minimal concentrations of glucose. Without a semipermeable membrane situated over the enzyme domain to control the flux of glucose and oxygen, a linear response to glucose levels can be obtained only up to about 40 mg/dL. However, in a clinical setting, a linear response to glucose levels is desirable up to at least about 500 mg/dL.

The resistance domain 44 includes a semipermeable membrane that controls the flux of oxygen and glucose to the underlying enzyme domain 46, preferably rendering oxygen in non-rate-limiting excess. As a result, the upper limit of linearity of glucose measurement is extended to a much higher value than that which is achieved without the resistance domain. In one embodiment, the resistance domain 44 exhibits an oxygen-to-glucose permeability ratio of approximately 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)). In some embodiments, a lower ratio of oxygen-to-glucose can be sufficient to provide excess oxygen by using a high oxygen soluble domain (for example, a silicone material) to enhance the supply/transport of oxygen to the enzyme membrane and/or electroactive surfaces. By enhancing the oxygen supply through the use of a silicone composition, for example, glucose concentration can be less of a limiting factor. In other words, if more oxygen is supplied to the enzyme and/or electroactive surfaces, then more glucose can also be supplied to the enzyme without creating an oxygen rate-limiting excess.

The resistance domain 44 is preferably formed from high oxygen soluble materials such as polymers formed from silicone, fluorocarbons, perfluorocarbons, or the like. In one embodiment, the resistance domain is formed from a silicone composition with a hydrophile such as such as polyethylene glycol, propylene glycol, pyrrolidone, esters, amides, carbonates, or polypropylene glycol covalently incorporated or grafted therein. In some alternative embodiments, the resistance domain is from polyurethane, for example, a polyurethane urea/polyurethane-block-polyethylene glycol blend.

In some embodiments, the resistance domain 44 can be formed as a unitary structure with the cell impermeable domain 42; that is, the inherent properties of the resistance domain 44 can provide the functionality described with reference to the cell impermeable domain 42 such that the cell impermeable domain 42 is incorporated as a part of resistance domain 44. In these embodiments, the combined resistance domain/cell impermeable domain can be bonded to or formed as a skin on the cell disruptive domain 40 during a molding process such as described above. In another embodiment, the resistance domain 44 is formed as a distinct layer and chemically or mechanically bonded to the cell disruptive domain 40 (if applicable) or the cell impermeable domain 42 (when the resistance domain is distinct from the cell impermeable domain).

In preferred embodiments, the thickness of the resistance domain is from about 10 microns or less to about 200 microns or more. In more preferred embodiments, the thickness of the resistance domain is from about 15, 20, 25, 30, or 35 microns to about 65, 70, 75, 80, 85, 90, 95, or 100 microns. In more preferred embodiments, the thickness of the resistance domain is from about 40 or 45 microns to about 50, 55, or 60 microns.

Enzyme Domain

An immobilized enzyme domain 46 is situated less distal from the electrochemically reactive surfaces than the resistance domain 44. In one embodiment, the immobilized enzyme domain 46 comprises glucose oxidase. In other embodiments, the immobilized enzyme domain 46 can be impregnated with other oxidases, for example, galactose oxidase, cholesterol oxidase, amino acid oxidase, alcohol oxidase, lactate oxidase, or uricase. For example, for an enzyme-based electrochemical glucose sensor to perform well, the sensor's response should neither be limited by enzyme activity nor cofactor concentration.

The enzyme domain 44 is preferably formed from high oxygen soluble materials such as polymers formed from silicone, fluorocarbons, perfluorocarbons, or the like. In one embodiment, the enzyme domain is formed from a silicone composition with a hydrophile such as such as polyethylene glycol, propylene glycol, pyrrolidone, esters, amides, carbonates, or polypropylene glycol covalently incorporated or grafted therein.

In one preferred embodiment, high oxygen solubility within the enzyme domain can be achieved by using a polymer matrix to host the enzyme within the enzyme domain, which has a high solubility of oxygen. In one exemplary embodiment of fluorocarbon-based polymers, the solubility of oxygen within a perfluorocarbon-based polymer is 50-volume %. As a reference, the solubility of oxygen in water is approximately 2-volume %.

Utilization of a high oxygen solubility material for the enzyme domain is advantageous because the oxygen dissolves more readily within the domain and thereby acts as a high oxygen soluble domain optimizing oxygen availability to oxygen-utilizing sources (for example, the enzyme and/or counter electrode). When the resistance domain 44 and enzyme domain 46 both comprise a high oxygen soluble material, the chemical bond between the enzyme domain 46 and resistance domain 44 can be optimized, and the manufacturing made easy.

In preferred embodiments, the thickness of the enzyme domain is from about 1 micron or less to about 40, 50, 60, 70, 80, 90, or 100 microns or more. In more preferred embodiments, the thickness of the enzyme domain is between about 1, 2, 3, 4, or 5 microns and 13, 14, 15, 20, 25, or 30 microns. In even more preferred embodiments, the thickness of the enzyme domain is from about 6, 7, or 8 microns to about 9, 10, 11, or 12 microns.

Interference Domain

The interference domain 48 is situated less distal to the implantable device than the immobilized enzyme domain. Interferants are molecules or other species that are electroreduced or electro-oxidized at the electrochemically reactive surfaces, either directly or via an electron transfer agent, to produce a false signal (for example, urate, ascorbate, or acetaminophen). In one embodiment, the interference domain 48 prevents the penetration of one or more interferants into the electrolyte phase around the electrochemically reactive surfaces. Preferably, this type of interference domain is much less permeable to one or more of the interferants than to the analyte.

In one embodiment, the interference domain 48 can include ionic components incorporated into a polymeric matrix to reduce the permeability of the interference domain to ionic interferants having the same charge as the ionic components. In another embodiment, the interference domain 48 includes a catalyst (for example, peroxidase) for catalyzing a reaction that removes interferants. U.S. Pat. No. 6,413,396 and U.S. Pat. No. 6,565,509 disclose methods and materials for eliminating interfering species; however in the preferred embodiments any suitable method or material can be employed.

In another embodiment, the interference domain 48 includes a thin membrane that is designed to limit diffusion of species, for example, those greater than 34 kD in molecular weight, for example. The interference domain permits analytes and other substances (for example, hydrogen peroxide) that are to be measured by the electrodes to pass through, while preventing passage of other substances, such as potentially interfering substances. In one embodiment, the interference domain 48 is constructed of polyurethane. In an alternative embodiment, the interference domain 48 comprises a high oxygen soluble polymer, such as described above.

In preferred embodiments, the thickness of the interference domain is from about 0.1 microns or less to about 10 microns or more. In more preferred embodiments, the thickness of the interference domain is between about 0.2, 0.3, 0.4, or 0.5 microns and about 5, 6, 7, 8, or 9 microns. In more preferred embodiments, the thickness of the interference domain is from about 0.6, 0.7, 0.8, 0.9, or 1 micron to about 2, 3, or 4 microns.

Electrolyte Domain

An electrolyte domain 50 is situated more proximal to the electrochemically reactive surfaces than the interference domain 48. To ensure the electrochemical reaction, the electrolyte domain 30 includes a semipermeable coating that maintains hydrophilicity at the electrochemically reactive surfaces of the sensor interface. The electrolyte domain 50 enhances the stability of the interference domain 48 by protecting and supporting the material that makes up the interference domain. The electrolyte domain also 50 assists in stabilizing the operation of the device by overcoming electrode start-up problems and drifting problems caused by inadequate electrolyte. The buffered electrolyte solution contained in the electrolyte domain also protects against pH-mediated damage that can result from the formation of a large pH gradient between the substantially hydrophobic interference domain and the electrodes due to the electrochemical activity of the electrodes. In some embodiments, the electrolyte domain may not be used, for example, when an interference domain is not provided.

In one embodiment, the electrolyte domain 50 includes a flexible, water-swellable, substantially solid gel-like film having a "dry film" thickness of from about 2.5 microns to about 12.5 microns, more preferably from about 3, 3.5, 4, 4.5, 5, or 5.5 to about 6, 6.5, 7, 7.5, 8, 8.5, 9, 9.5, 10, 10.5, 11, 11.5, or 12 microns. "Dry film" thickness refers to the thickness of a cured film cast from a coating formulation onto the surface of the membrane by standard coating techniques.

In some embodiments, the electrolyte domain 50 is formed of a curable mixture of a urethane polymer and a hydrophilic polymer. Particularly preferred coatings are formed of a polyurethane polymer having anionic carboxylate functional groups and non-ionic hydrophilic polyether segments, which is crosslinked in the presence of polyvinylpyrrolidone and cured at a moderate temperature of about 50° C. In some preferred embodiments, the electrolyte domain 50 is formed from high oxygen soluble materials such as polymers formed from silicone, fluorocarbons, perfluorocarbons, or the like.

In one preferred embodiment, the electrolyte domain 50 is formed from a high oxygen soluble material, such as described above. In preferred embodiments, the thickness of the electrolyte domain is from about 1 micron or less to about 40, 50, 60, 70, 80, 90, or 100 microns or more. In more preferred embodiments, the thickness of the electrolyte domain is from about 2, 3, 4, or 5 microns to about 15, 20, 25, or 30 microns. In even more preferred embodiments, the thickness of the electrolyte domain is from about 6, 7, or 8 microns to about 9, 10, 11, or 12 microns.

Underlying the electrolyte domain is an electrolyte phase is a free-fluid phase including a solution containing at least one compound, typically a soluble chloride salt, which conducts electric current. In one embodiment wherein the membrane system is used with a glucose sensor such as is described herein, the electrolyte phase flows over the electrodes and is in contact with the electrolyte domain. The devices of the preferred embodiments contemplate the use of any suitable electrolyte solution, including standard, commercially available solutions. Generally, the electrolyte phase can have the same osmotic pressure or a lower osmotic pressure than the sample being analyzed. In preferred embodiments, the electrolyte phase comprises normal saline.

In various embodiments, any of these domains can be omitted, altered, substituted for, and/or incorporated together without departing from the spirit of the preferred embodiments. For example, a distinct cell impermeable domain may not exist. In such embodiments, other domains accomplish the function of the cell impermeable domain. As another example, the interference domain can be eliminated in certain embodiments wherein two-electrode differential measurements are employed to eliminate interference, for example, one electrode being sensitive to glucose and electrooxidizable interferants and the other only to interferants, such as is described in U.S. Pat. No. 6,514,718. In such embodiments, the interference domain can be omitted.

A variety of configurations are contemplated with the membrane systems of the preferred embodiments, however the exemplary configurations are not meant to be limiting and may be modified within the scope of the preferred embodiments. In one embodiment, the enzyme domain is formed from a material with a high oxygen solubility, which is believed to optimize oxygen availability to the enzyme immobilized therein. In another embodiment, all domains between the fluid supply (for example, interstitial fluid) and the enzyme (up to and including the enzyme domain) are formed from a material with a high oxygen solubility, which is believed to dynamically retain a substantially continuous path of high oxygen availability to the enzyme and/or electroactive surfaces during local ischemic periods. In yet another embodiment, all domains of a membrane system are formed from high oxygen soluble materials; in this way, the membrane system transports and/or maintains high oxygen availability substantially continuously across the membrane system, from the interstitial fluid to the implantable device surface, providing increased oxygen availability to the implantable device, for example electroactive surfaces thereon or transplanted cells located therein. While not wishing to be bound by theory, it is believed that maintaining high oxygen availability at the interface of the implantable device improves device performance even during transient ischemia and other low oxygen situations.

Reference is now made to FIGS. 5A and 5B, which are schematic diagrams of oxygen concentration profiles through a prior art membrane (FIG. 5A) and a membrane system of the preferred embodiments (FIG. 5B). FIG. 5A illustrates a fluid source 52, such as interstitial fluid within the subcutaneous space, which provides fluid to a membrane system 54*a*. The membrane system 54*a* is a conventional membrane, for example, formed from a polyurethane-based or other non-high oxygen soluble material. An oxygen-utilizing source 56, such as the immobilized enzyme within the enzyme domain 46 or electroactive surfaces 16 described herein, utilizes oxygen from the fluid as a catalyst or in an electrochemical reaction. In some alternative embodiments, the oxygen-utilizing source 56 comprises cells within a cell transplantation device, which utilize oxygen in the fluid for cellular processes.

The upper dashed lines represent oxygen concentration in the fluid source ($C_f$) and oxygen concentration in the membrane system ($C_m$) at equilibrium (namely, without oxygen utilization) under normal conditions. However, when the membrane system 54*a* interfaces with an oxygen-utilizing source 56, oxygen concentration within the membrane system will be utilized. Accordingly, line 58*a* represents oxygen concentration under normal conditions decreasing at steady state as it passes through the membrane system 54*a* to the oxygen-utilizing source 56. While not wishing to be bound by theory, the oxygen concentration at the interface between the membrane system 54*a* and the oxygen-utilizing source 56 provides sufficient oxygen under normal conditions for oxygen-utilizing sources in vivo, such as enzymatic reactions, cellular processes, and electroactive surfaces.

Unfortunately, "normal conditions" do not always occur in vivo, for example during transient ischemic periods, such as described in more detail above with reference to FIG. 3. During "ischemic conditions," oxygen concentration is decreased below normal to a concentration as low as zero. Accordingly, line 60*a* represents oxygen concentration during an ischemic period, wherein the oxygen concentration of the fluid source ($C_f$) is approximately half of its normal concentration. A linear relationship exists between the fluid source oxygen concentration ($C_f$) and the membrane system oxygen concentration ($C_m$) (see Hitchman, M. L. Measurement of Dissolved Oxygen. In *Chemical Analysis*; Elving, P., Winefordner, J., Eds.; John Wiley & Sons: New York, 1978; Vol. 49, pp. 63-70). Accordingly, line 62*a* represents the oxygen concentration within the membrane system during the ischemic period, which is approximately half of its normal concentration. Unfortunately, the resulting oxygen concentration at the interface of the membrane 54*a* and oxygen-utilizing source 56 is approximately zero. While not wishing to bound by any particular theory, it is believed that the oxygen concentration at the interface between the conventional membrane system 54*a* and the oxygen-utilizing source 56 does not provide sufficient oxygen for oxygen-utilizing sources in vivo, such as enzymatic reactions, cellular processes, and electroactive surfaces, during some ischemic conditions.

Referring to FIG. 5B, a fluid source 52, such as interstitial fluid within the subcutaneous space, provides fluid to a membrane system 54*b*. The membrane system 54*b* is a membrane system of the preferred embodiments, such as an enzyme domain 46 or an entire membrane system formed from a high oxygen soluble material such as described herein, through which the fluid passes. An oxygen-utilizing source 56, such as the immobilized enzyme described herein, utilizes oxygen from the fluid as a catalyst. In some alternative embodiments, the oxygen-utilizing source 56 comprises cells within a cell transplantation device, which utilize oxygen in the fluid for cellular processes. In some alternative embodiments, the oxygen-utilizing source 56 comprises an electroactive surface that utilizes oxygen in an electrochemical reaction.

The upper dashed lines represent oxygen concentration in the fluid source ($C_f$) and oxygen concentration in the membrane system ($C_m$) at equilibrium (namely, without oxygen utilization) under normal conditions. The membrane system of the preferred embodiments 54*b* is illustrated with a significantly higher oxygen concentration than the conventional membrane 54*a*. This higher oxygen concentration at equilibrium is attributed to higher oxygen solubility inherent in the properties of the membrane systems of the preferred embodiments as compared to conventional membrane materials. Line 58*b* represents oxygen concentration under normal conditions decreasing at steady state as it passes through the membrane system 54*b* to the oxygen-utilizing source 56. While not wishing to be bound by theory, the oxygen concentration at the interface between the membrane system 54*b* and the oxygen-utilizing source 56 is believe to provide sufficient oxygen under normal conditions for oxygen-utilizing sources in vivo, such as enzymatic reactions, cellular processes, and electroactive surfaces.

Such as described above, "normal conditions" do not always occur in vivo, for example during transient ischemic periods, wherein oxygen concentration is decreased below normal to a concentration as low as zero. Accordingly, line 60*b* represents oxygen concentration during ischemic conditions, wherein the oxygen concentration of the fluid source ($C_f$) is approximately half of its normal concentration. Because of the linear relationship between the fluid source oxygen concentration ($C_f$) and the membrane system oxygen concentration ($C_m$), the membrane system oxygen concentration, which is represented by a line 62*b*, is approximately half of its normal concentration. In contrast to the conventional membrane 62*a* illustrated in FIG. 5A, however, the high oxygen solubility of the membrane system of the preferred embodiments dynamically retains a higher oxygen availability within the membrane 54*b*, which can be utilized during ischemic periods to compensate for oxygen deficiency, illustrated by sufficient oxygen concentration 62*b* provided at the interface of the membrane 54*b* and oxygen-utilizing source 56. Therefore, the high oxygen solubility of the membrane systems of the preferred embodiments enables device function even during transient ischemic periods.

Methods and devices that are suitable for use in conjunction with aspects of the preferred embodiments are disclosed in co-pending U.S. patent application Ser. No. 10/842,716, filed May 10, 2004 and entitled, "MEMBRANE SYSTEMS INCORPORATING BIOACTIVE AGENTS"; co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; U.S. application Ser. No. 10/685,636 filed Oct. 28, 2003 and entitled, "SILICONE COMPOSITION FOR MEMBRANE SYSTEM"; U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE SENSOR DATA"; U.S. Pat. No. 6,702,857 entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE"; U.S. application Ser. No. 60/489,615 filed Jul. 23, 2003 and entitled "ROLLED ELECTRODE ARRAY AND ITS METHOD FOR MANUFACTURE"; U.S. application Ser. No. 60/490,010 filed Jul. 25, 2003 and entitled "INCREASING BIAS FOR OXYGEN PRODUCTION IN AN ELECTRODE ASSEMBLY"; U.S. application Ser. No. 60/490,208 filed Jul. 25, 2003 and entitled "ELECTRODE ASSEMBLY WITH INCREASED OXYGEN GENERATION"; U.S. application Ser. No. 60/490,007 filed Jul. 25, 2003 and entitled "OXYGEN-GENERATING ELECTRODE FOR USE IN ELECTROCHEMICAL SENSORS"; U.S. application Ser. No. 10/896,637 filed on Jul. 21, 2004 and entitled "ROLLED ELECTRODE ARRAY AND ITS METHOD FOR MANUFACTURE"; U.S. application Ser. No. 10/896,772 filed on Jul. 21, 2004 and entitled "INCREASING BIAS FOR OXYGEN PRODUCTION IN AN ELECTRODE ASSEMBLY"; U.S. application Ser. No. 10/897,377 filed on Jul. 21, 2004 and entitled "ELECTRODE ASSEMBLY WITH INCREASED OXYGEN GENERATION"; U.S. application Ser. No. 10/897,312 filed on Jul. 21, 2004 and entitled "ELECTRODE SYSTEMS FOR ELECTROCHEMICAL SENSORS". The foregoing patent applications and patents are incorporated herein by reference in their entireties.

All references cited herein are incorporated herein by reference in their entireties. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. An implantable device for continuous in vivo measurement of an analyte concentration in a host, the device comprising:

a sensor configured for implantation in a host, the sensor configured to operatively connect with electronic circuitry configured to generate a signal associated with a concentration of an analyte in a host; and a membrane located over the sensor and configured to control a flux of oxygen and the analyte therethrough, wherein the membrane comprises a material having an oxygen permeability of from about 5 Barrers to about 1000 Barrers.

2. The device of claim 1, wherein the material comprises a copolymer comprising a fluorocarbon segment.

3. The device of claim 2, wherein the fluorocarbon segment is perfluorinated.

4. The device of claim 2, wherein the copolymer further comprises a polycarbonate segment.

5. The device of claim 2, wherein the copolymer has an oxygen solubility of about 50-volume %.

6. The device of claim 2, wherein the membrane comprises a blend, wherein the blend comprises the copolymer and a hydrophilic polymer.

7. The device of claim 6, wherein the hydrophilic polymer is selected from the group consisting of polyvinylpyrrolidone, polyhydroxyethyl methacrylate, polyvinylalcohol, polyacrylic acid, polyethers, and copolymers thereof.

8. The device of claim 1, wherein the membrane has a thickness of from about 3 microns to about 65 microns.

9. The device of claim 1, wherein the membrane comprises an enzyme domain, wherein the enzyme domain comprises an enzyme configured to react with the analyte.

10. The device of claim 1, wherein the membrane is configured to limit or block passage of interfering species therethrough.

11. The device of claim 1, wherein the membrane is configured to provide protection to the sensor from a biological environment.

12. The device of claim 1, wherein the material has an oxygen permeability of at least about 10 Barrers.

13. The device of claim 1, wherein the material has an oxygen permeability of at least about 100 Barrers.

14. The device of claim 1, wherein the material has an oxygen permeability of at least about 500 Barrers.

15. The device of claim 1, wherein the material has an oxygen permeability of at least about 800 Barrers.

16. The device of claim 1, wherein the analyte is glucose.

17. The device of claim 1, wherein the membrane has an oxygen permeability from about 30 Barrers to about 1000 Barrers.

18. The device of claim 1, wherein the membrane comprises a domain that has an oxygen permeability from about 30 Barrers to about 1000 Barrers.

19. The device of claim 1, wherein the material has an oxygen solubility that is from about three times to about ten times greater than an oxygen solubility of aqueous media.

20. An implantable device for continuous in vivo measurement of a glucose concentration in a host, the device comprising:

a sensor operatively connected to electronic circuitry configured to generate a signal associated with a concentration of glucose in a host; and a membrane located over the sensor and configured to control a flux of oxygen and glucose therethrough, wherein the membrane comprises a material having an oxygen permeability of from about 5 Barrers to about 1000 Barrers, wherein the material comprises a copolymer comprising a fluorocarbon segment and a polycarbonate segment, wherein the membrane has a thickness of from about 3 microns to about 65 microns, and wherein the membrane comprises an enzyme domain comprising an enzyme configured to react with glucose.

21. The device of claim 20, wherein the material has an oxygen solubility that is from about three times to about ten times greater than an oxygen solubility of aqueous media.

* * * * *

UNITED STATES PATENT AND TRADEMARK OFFICE

CERTIFICATE OF CORRECTION

PATENT NO. : 8,255,030 B2
APPLICATION NO. : 11/410555
DATED : August 28, 2012
INVENTOR(S) : Petisce et al.

It is certified that error appears in the above-identified patent and that said Letters Patent is hereby corrected as shown below:

| Issued Patent Column | Line | Description of Discrepancy |
|---|---|---|
| (Item 56) Page 6 Col. 1 | 62 | Under Other Publications, change “artifical” to --artificial--. |
| (Item 56) Page 6 Col. 1 | 73 | Under Other Publications, change ““xenogenic.”” to --“xenogeneic.”--. |
| (Item 56) Page 6 Col. 1 | 75 | Under Other Publications, change “xenogenic.” to --xenogeneic.--. |
| (Item 56) Page 6 Col. 2 | 6 | Under Other Publications, change “hypoglycaemic” to --hypoglycemic--. |
| (Item 56) Page 6 Col. 2 | 20 | Under Other Publications, change “Thechnol.” to --Technol.--. |
| (Item 56) Page 6 Col. 2 | 58 | Under Other Publications, change “basedon” to --based--. |
| (Item 56) Page 7 Col. 1 | 72 | Under Other Publications, change “-impintable,” to -- -implantable,--. |
| (Item 56) Page 7 Col. 1 | 4 | Under Other Publications, change “reliablity” to --reliability--. |
| (Item 56) Page 7 Col. 1 | 15 | Under Other Publications, change “Enzymlology,” to --Enzymology,--. |

Signed and Sealed this
Twenty-sixth Day of March, 2013

Teresa Stanek Rea
*Acting Director of the United States Patent and Trademark Office*

| | | |
|---|---|---|
| (Item 56) Page 7 Col. 1 | 24 | Under Other Publications, change "artifical" to --artificial--. |
| (Item 56) Page 7 Col. 1 | 36 | Under Other Publications, change "your and your" to --you and your--. |
| (Item 56) Page 7 Col. 1 | 49 | Under Other Publications, change "glocuse" to --glucose--. |
| (Item 56) Page 7 Col. 1 | 50 | Under Other Publications, change "Diabetese" to --Diabetes--. |
| (Item 56) Page 7 Col. 1 | 63 | Under Other Publications, change "Hypoglycaemia-" to --Hypoglycemia- --. |
| (Item 56) Page 7 Col. 2 | 3 | Under Other Publications, change "Thechnol." to --Technol.--. |
| (Item 56) Page 7 Col. 2 | 6 | Under Other Publications, change "VIA@" to --VIA®--. |
| (Item 56) Page 7 Col. 2 | 8 | Under Other Publications, change "Diabetese" to --Diabetes--. |
| (Item 56) Page 7 Col. 2 | 27 | Under Other Publications, change "inactiviation" to --inactivation--. |
| (Item 56) Page 7 Col. 2 | 41 | Under Other Publications, change "patents" to --patients--. |
| (Item 56) Page 8 Col. 1 | 12 | Under Other Publications, change "Aniodic" to --Anodic--. |
| (Item 56) Page 8 Col. 1 | 60 | Under Other Publications, change "activitiy," to --activity,--. |
| (Item 56) Page 8 Col. 2 | 2 | Under Other Publications, change "Beioelectronics," to --Bioelectronics,--. |
| (Item 56) Page 8 Col. 2 | 3 | Under Other Publications, change "glocuse" to --glucose--. |
| (Item 56) Page 8 Col. 2 | 12 | Under Other Publications, change "valication" to --validation--. |

| | | |
|---|---|---|
| (Item 56)<br>Page 8<br>Col. 2 | 13 | Under Other Publications,<br>change "iunsulin interaaction in tyhpe 1"<br>to --insulin interaction in type 1--. |
| (Item 56)<br>Page 8<br>Col. 2 | 26 | Under Other Publications,<br>change "Electronanalysis"<br>to --Electroanalysis--. |
| (Item 56)<br>Page 8<br>Col. 2 | 41 | Under Other Publications,<br>change "artifical" to --artificial--. |
| (Item 56)<br>Page 8<br>Col. 2 | 50 | Under Other Publications,<br>change "amperometeric"<br>to --amperometric--. |
| (Item 56)<br>Page 8<br>Col. 2 | 57 | Under Other Publications,<br>change "Thechnol." to --Technol.--. |
| (Item 56)<br>Page 9<br>Col. 1 | 17 | Under Other Publications,<br>change "termistor" to --thermistor--. |
| (Item 56)<br>Page 9<br>Col. 1 | 18 | Under Other Publications,<br>change "metobolites," to --metabolites,--. |
| (Item 56)<br>Page 9<br>Col. 1 | 20 | Under Other Publications,<br>change "cholesteral and cholesteral"<br>to --cholesterol and cholesterol--. |
| (Item 56)<br>Page 9<br>Col. 1 | 22 | Under Other Publications,<br>change "Apllied" to --Applied--. |
| (Item 56)<br>Page 9<br>Col. 2 | 16 | Under Other Publications,<br>change "Subcutaenous"<br>to --Subcutaneous--. |
| (Item 56)<br>Page 9<br>Col. 2 | 22 | Under Other Publications,<br>change "assitance" to --assistance--. |
| (Item 56)<br>Page 9<br>Col. 2 | 23 | Under Other Publications,<br>change "Thechnol." to --Technol.--. |
| (Item 56)<br>Page 9<br>Col. 2 | 63 | Under Other Publications,<br>change "pancrease" to --pancreas--. |
| (Item 56)<br>Page 9<br>Col. 2 | 73 | Under Other Publications,<br>change "Thechnol." to --Technol.--. |
| (Item 56)<br>Page 10<br>Col. 1 | 17 | Under Other Publications,<br>change "cholesteral" to --cholesterol--. |

| | | |
|---|---|---|
| (Item 56) Page 10 Col. 1 | 34 | Under Other Publications, change "Deabetes" to --Diabetes--. |
| (Item 56) Page 10 Col. 1 | 53 | Under Other Publications, change "Tranducers" to --Transducers--. |
| (Item 56) Page 12 Col. 1 | 31 | Under Other Publications, change "Bromedical" to --Biomedical--. |
| (Item 56) Page 12 Col. 2 | 50 | Under Other Publications, change "Senso" to --Sensor--. |
| (Item 56) Page 13 Col. 1 | 42 | Under Other Publications, change "Membran," to --Membrane,--. |
| (Item 56) Page 13 Col. 2 | 16 | Under Other Publications, change "Membrance" to --Membrane--. |
| 4 | 8 | Change "andrenostenedione;" to --androstenedione;--. |
| 4 | 10 | Change "camitine;" to --carnitine;--. |
| 4 | 10 | Change "camosinase;" to --carnosinase;--. |
| 4 | 23 | Change "diptheria/" to --diphtheria/--. |
| 4 | 30 | Change "perioxidase;" to --peroxidase;--. |
| 4 | 39 | Change "sissomicin;" to --sisomicin;--. |
| 4 | 43 | Change "duodenalisa," to --duodenalis,--. |
| 4 | 51 | Change "Trepenoma pallidium," to --Treponema pallidum,--. |
| 4 | 52 | Change "stomatis" to --stomatitis--. |
| 5 | 6 | Change "(barbituates," to --(barbiturates,--. |
| 5 | 43 | Change "by product," to --byproduct,--. |
| 7 | 17 | Change "(degree, Centigrade)." to --(degree Centigrade).--. |
| 7 | 56 | Change "Ward el al.;" to --Ward et al.;--. |
| 8 | 1 | Change "there" to --their--. |
| 9 | 11 | Change "O2)." to --($O_2$).--. |
| 13 | 32 | Change "10/685,636" to --10/695,636--. |
| 13 | 33 | Change "FOR MEMBRANE SYSTEM,"" to --FOR BIOCOMPATIBLE MEMBRANE,"--. |
| 20 | 61 | Change "10/685,636" to --10/695,636--. |
| 20 | 62 | Change "FOR MEMBRANE SYSTEM";" to --FOR BIOCOMPATIBLE MEMBRANE";--. |

| | | |
|---|---|---|
| 21 | 48-49 | Change ““ELECTRODE ASSEMBLY” to --“ELECTROCHEMICAL SENSORS INCLUDING ELECTRODE SYSTEMS--. |